US007396537B1

(12) United States Patent
Krupnick et al.

(10) Patent No.: US 7,396,537 B1
(45) Date of Patent: Jul. 8, 2008

(54) CELL DELIVERY PATCH FOR MYOCARDIAL TISSUE ENGINEERING

(75) Inventors: Alexander Krupnick, Philadelphia, PA (US); Daniel Kreisel, Philadelphia, PA (US); Bruce R. Rosengard, Gladwyne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 120 days.

(21) Appl. No.: 10/378,015

(22) Filed: Feb. 28, 2003

Related U.S. Application Data

(60) Provisional application No. 60/408,448, filed on Sep. 5, 2002, provisional application No. 60/360,820, filed on Feb. 28, 2002.

(51) Int. Cl.
*A61K 9/00* (2006.01)
(52) U.S. Cl. .................. 424/400; 424/443; 424/444; 424/93.1
(58) Field of Classification Search ................ 424/400, 424/443, 444, 93.1
See application file for complete search history.

(56) References Cited

U.S. PATENT DOCUMENTS

| | | | | | |
|---|---|---|---|---|---|
| 5,716,404 | A | * | 2/1998 | Vacanti et al. | 623/8 |
| 5,749,895 | A | * | 5/1998 | Sawyer et al. | 606/214 |
| 5,855,610 | A | * | 1/1999 | Vacanti et al. | 623/2.13 |
| 6,497,729 | B1 | * | 12/2002 | Moussy et al. | 623/23.57 |
| 6,726,696 | B1 | * | 4/2004 | Houser et al. | 606/151 |
| 2003/0040113 | A1 | * | 2/2003 | Mizuno et al. | 435/395 |

OTHER PUBLICATIONS

Asfour, B., et al., "A simple new model of physiologically working heterotopic rat heart transplantation provides hemodynamic performance equivalent to that of an orthotopic heart," *J. Heart & Lung Transplantation*, 1999, 18(10), 927-936.
Bruder, S.P., et al., "The effect of implants loaded with autologous mesenchymal stem cells on the healing of canine segmental bone defects," *J. of Bone & Joint Surgery*, American Volume, 1998, 80A(7), 985-996.
Carrier, R.L., et al., "Cardiac tissue engineering: cell seeding, cultivation parameters, and tissue construct characterization," *Biotechnology & Bioengineering*, Sep. 5, 1999, 64(5), 580-589.
Cassell, O.C., et al., "The influence of extracellular matrix on the generation of vascularized, engineered, transplantable tissue," *Annals of the New York Academy of Sciences*, 2001, 944, 429-442.
Fishman, N.H., et al., "Models of congenital heart disease in fetal lambs," *Circulation*, Aug. 1978, 58(2), 354-364.
Grigoriadis, A.E., et al., "Differentiation of muscle, fat, cartilage, and bone from stem cells present in a bone-derived clonal cell population: effect of dexamethasone," *J. of Cell Biology*, Jun. 1988, 106(6), 2139-2151.
Hoerstrup, S.P., et al., "Functional living trileaflet heart valves grown in vitro," *Circulation*, 2000, 102(suppl. III), III-44-III-49.

Juang, J.H., et al., Outcome of subcutaneous islet transplantation improved by polymer device, *Transplantation*, Jun. 15, 1996, 61, 1557-1561.
Kaihara S., et al., "Tissue engineering: toward new solutions for transplantation and reconstructive surgery," *Archives of Surgery*, Nov. 1999, 134, 1184-1188.
Klug, M.G., et al., "Genetically selected cardiomyocytes from differentiating embryonic stem cells form stable intracardiac grafts," *J. Clinical Investigation*, Jul. 1996, 98(1), 216-224.
Koh, T., et al., "Stable fetal cardiomyocyte grafts in the hearts of dystrophic mice and dogs," *J. Clin. Invest.*, Oct. 1995, 96, 2034-2042.
Kreisel, D., et al., "A simple method for culturing mouse vascular endothelium," *J. of Immunological Methods*, 2001, 254, 31-45.
Kreisel, D., et al., "Non-hematopoietic allograft cells directly activate CD8+ T cells and trigger acute rejection: an alternative mechanism of allorecognition," *Nature Medicine*, 2002, 8, 233-239.
Krupnick, A., et al., "A novel small animal model of ventricular tissue engineering," *J. of Heart & Lung Transplantation*, Feb. 2002, 21(2), 233-243.
Krupnick, et al., "Multiparameter flow cytometric approach for simultaneous evaluation of T lymphocyte-endothelial cell interactions," *Cytometry (Communications in Clinical Cytometry)*, 2001, 46, 271-280.
Li, R.K., et al., "Smooth muscle cell transplantation into myocardial scar tissue improves heart function," *J. of Molecular & Cellular Cardiology*, 1999, 31, 513-522.
Makino, S., et al., "Cardiomyocytes can be generated from marrow stromal cells in vitro," *J. of Clinical Investigation*, Mar. 1999, 103(5), 697-705.
Malouf, N.N., et al., "Adult-derived stem cells from the liver become myocytes in the heart in vivo," *American J. of Pathology*, Jun. 2001, 158(6), 1929-1935.
Mooney, D.J., et al., "Fabricating tubular devices from polymers of lactic and glycolic acid for tissue engineering," *Tissue Engineering*, 1995, 1(2), 107-118.
Niklason, L.E., et al., "Functional arteries grown in vitro," *Science*, Apr. 16, 1999, 284, 489-493.
Ono, K., et al., "Improved technique of heart transplantation in rats," *J of Thoracic & Cardiovascular Surgery*, Feb. 1969, 57(2), 225-229.
Orlic, D., et al., "Bone marrow cells regenerate infracted myocardium," *Nature*, Apr. 5, 2001, 410, 701-705.
Osses, N., et al., "ECM is required for skeletal muscle differentiation independently of muscle regulatory factor expression," *Am. J. of Physiology Cell Physiology*, 2002, 282(2) C383-C394.

(Continued)

*Primary Examiner*—Ruth A Davis
(74) *Attorney, Agent, or Firm*—Woodcock Washburn LLP

(57) ABSTRACT

A patch for cardiac tissue engineering includes a gel layer supported by an intermediate layer, which is attached to a reinforcement layer. These patches may be implanted in a heart to treat pediatric congenital malformations of the heart as well as adult ischemic myopathies. The gel layer may include cells such as, for example, stem cells; the intermediate layer may be biodegradable porous mesh and the reinforcement layer may be polytetrafluoroethylene. Included are methods for making patches according to the invention and for tissue engineering using patches of the invention.

17 Claims, 27 Drawing Sheets

OTHER PUBLICATIONS

Peters, M.C., et al., Synthetic extracellular matrices for cell transplantation, in: Liu, D.M., et al. (Eds.), *Materials Science Forum, Switzerland: Trans Tech Publications*, 1997, 250, 43-52.

Pittenger, M.F., et al., "Multilineage potential of adult human mesenchymal stem cells," *Science*, Apr. 2, 1999, 284, 143-147.

Prockop, D.J., "Marrow stromal cells as stem cells for nonhematopoetic tissues," *Science*, Apr. 4, 1997, 276, 71-74.

Sakai, T., et al., "Autologous heart cell transplantation improves cardiac function after myocardial injury," *Annals of Thoracic Surgery*, 1999, 68, 2074-2081.

Sakata, J., et al., "Tracheal composites tissue engineered from chondrocytes, tracheal epithelial cells, and synthetic degradable scaffolding," *Transplantation Proceedings*, Dec. 1994, 26(6), 3309-3310.

Schiller, N.B., et al., "Recommendations for quantitation of the left venticle by two-dimensional echocardiography," *J. American Society of Echocardiography*, Sep.-Oct. 1989, 2(5), 358-367.

Seale, P., et al., "Pax7 is required for the specification of myogenic satellite cells," *Cell*, Sep. 15, 2000, 102, 777-786.

Shinoka, T., et al., "Tissue engineering heart valves: valve leaflet replacement study in a lamb model," *Annals of Thoracic Surgery*, 1995, 60, S513-S516.

Solchaga, L.A., et al., "High variability in rabbit bone marrow-derived mesenchymal cell preparations," *Cell Transplantation*, 1999, 8, 511-519.

Toma, C., et al., "Human mesenchymal stem cells differentiate to a cardiomyocyte phenotype in the adult murine heart," *Circulation*, Jan. 2002, 105(1), 93-98.

Wakitani, S., et al., "Myogenic cells derived from rat bone marrow mesenchymal stem cells exposed to 5-azacytidine," *Muscle & Nerve*, Dec. 1995, 18(12), 1417-1426.

Wobus, A.M., "Development of cardiomyocytes expressing cardiac-specific genes, action potentials, and ionic channels during embryonic stem cell-derived cardiogenesis," *Annals of the New York Academy of Sciences*, 1995, 752, 460-469.

Zimmermann, W.H., et al., "Three-dimensional engineered heart tissue from neonatal rat cardiac myocytes," *Biotechnology & Bioengineering*, Apr. 5, 2000, 68(1), 106-114.

* cited by examiner

Non-Functioning Left Ventricle

Functioning Left Ventricle

Fig. 10e Fig. 10g
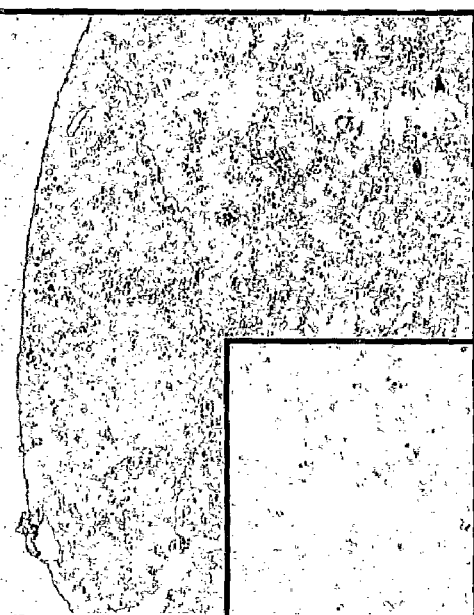
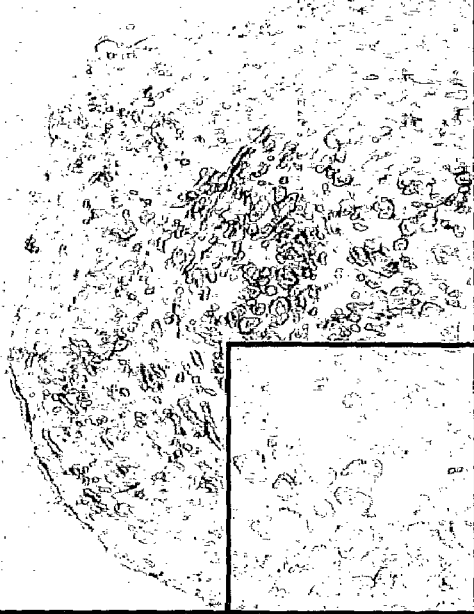
Fig. 10d Fig. 10f

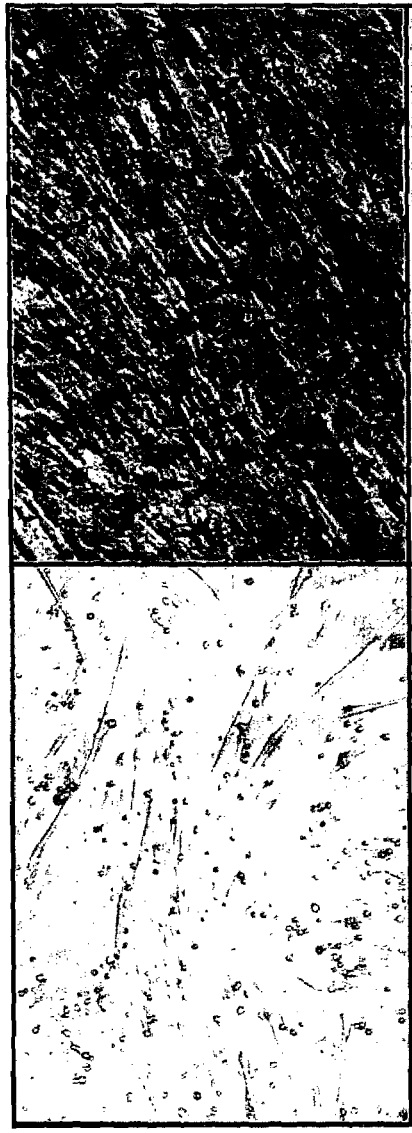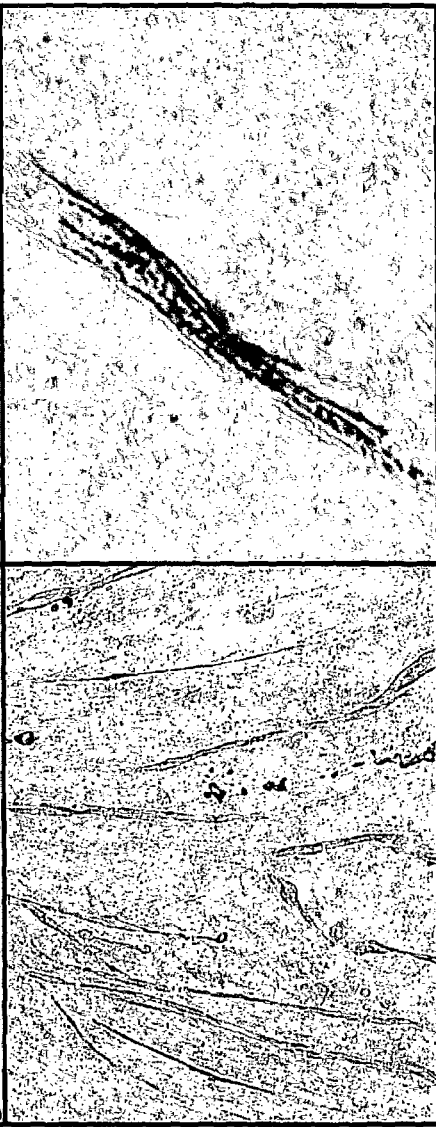
Fig. 11b  Fig. 11c  Fig. 11d  Fig. 11e

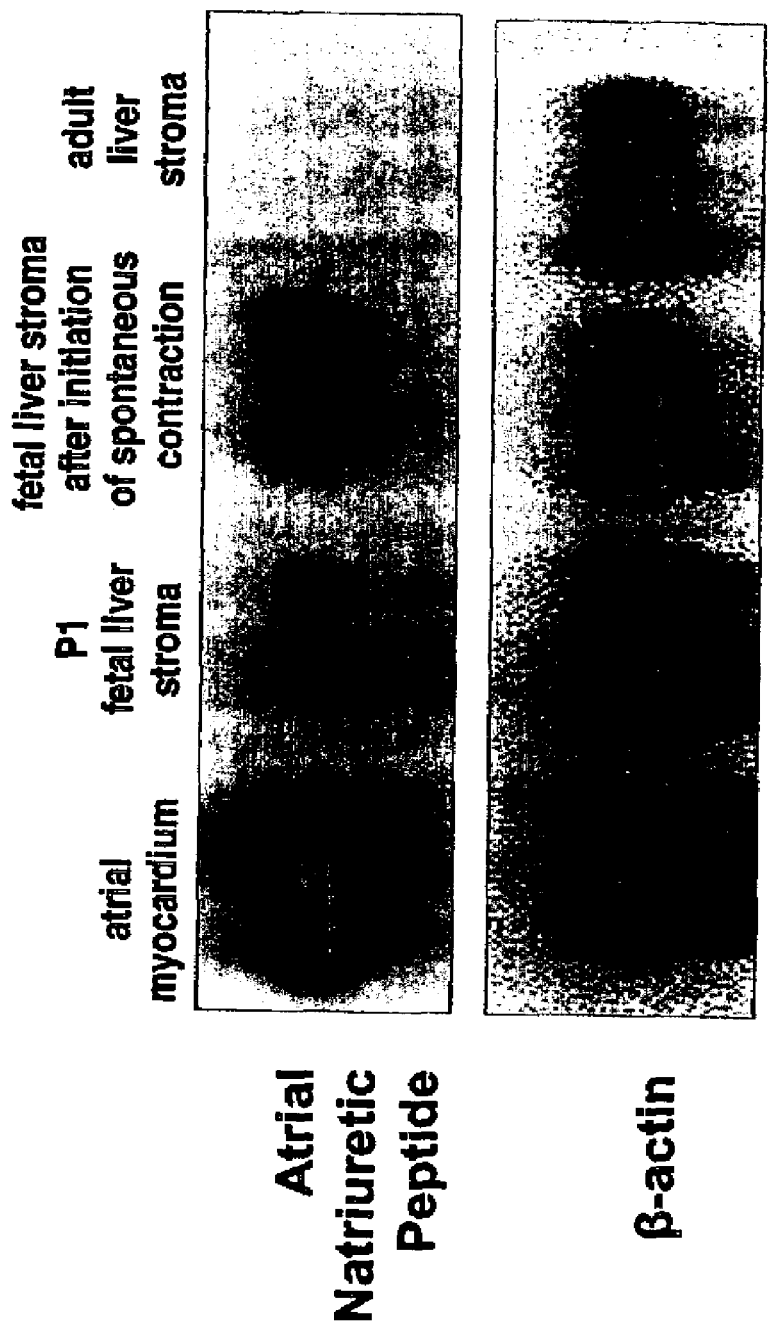

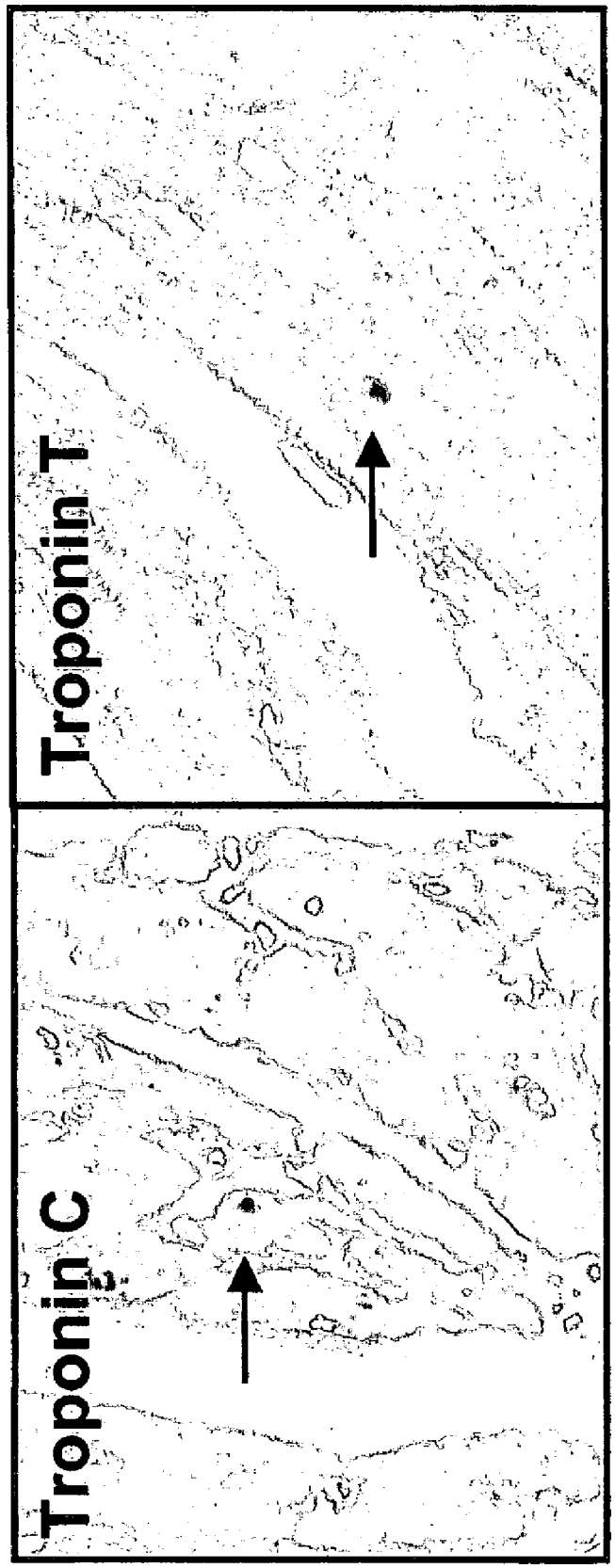

CELL DELIVERY PATCH FOR MYOCARDIAL TISSUE ENGINEERING

CROSS-REFERENCE TO RELATED APPLICATIONS

The present patent application claims the benefit of the filing dates of U.S. Provisional Patent Application Ser. No. 60/360,820, filed Feb. 28, 2002 and U.S. Provisional Patent Application Ser. No. 60/408,448, filed Sep. 5, 2002, both of which are hereby incorporated by reference in their entireties.

GOVERNMENT SUPPORT

The present invention was supported by the U.S. National Institutes of Health under Grant No. NIH NRSA F32-HL10251. The government may have certain rights in the invention.

FIELD OF THE INVENTION

The present invention is directed to a cell delivery patch used for cardiac tissue engineering, as well as to a method for cardiac tissue engineering using such a patch.

BACKGROUND OF THE INVENTION

Congenital heart defects are the most common form of birth anomalies, affecting 6 to 8 patients per 1000 births, and are the leading non-infectious cause of death in children. Hypoplastic left heart syndrome is the most devastating of these conditions and is characterized by marked hypoplasia or atresia of the left ventricle as well as hypoplasia of the ascending aorta and aortic valve. Palliation of this disease can be achieved through either a staged reconstruction, converting the cardiovascular system to a single ventricle based pump, or cardiac transplantation. Both of these procedures carry significant risks with undetermined long-term effects.

Advances in fetal imaging have made possible the early gestational diagnosis of most anatomic congenital anomalies. Advances in prenatal intervention and fetal tissue sampling have resulted in consideration of the strategy of perinatal tissue engineering: i.e. the prenatal harvest, isolation, and in vitro expansion of autologous fetal cells for the purpose of engineering a tissue construct with subsequential surgical reconstruction immediately after birth. To date this concept has been explored as an experimental therapeutic strategy for reconstruction of muscular diaphragmatic defects, bladder exstrophy, as well as superficial skin defects.

With respect to adults, despite tremendous advances in the treatment of acute myocardial infarction, post-infarction congestive heart failure remains a difficult clinical problem. Coronary occlusion with consequent regional ischemia leads to loss of cardiomyocytes and progressive replacement of muscle by collagenous tissue resulting in a myocardial scar. Even a small scar progressively expands, directly affecting the contractile function of adjacent border zone myocardium and overall global contractile function. Thus, left ventricular dilatation and heart failure can occur even after a myocardial infarction of moderate size. While novel therapeutic strategies such as biventricular pacing, mitral valve repair and ventricular remodeling surgery may improve the quality of life in a portion of patients with end-stage heart failure, heart transplantation is still the only available treatment that significantly lengthens life expectancy. Transplantation, however, is limited by a chronic shortage of donor hearts.

Treatment by transplantation is also limited by the problem of rejection. Advances in immunosuppression have significantly improved the treatment of acute rejection but chronic rejection in the form of cardiac allograft vasculopathy remains a leading cause of death in transplant recipients. Organ rejection can be initiated by two separate pathways of allorecognition. Unlike physiologic "indirect" T cell mediated allorecognition, where a foreign antigen (in this case an alloantigen) is processed and presented by a recipient antigen presenting cell to a recipient T cell in an MHC self-restricted manner, "direct allorecognition" is driven by the recognition of the intact alloantigen on an allogeneic antigen presenting cell. Due to this molecular mimicry, the precursor frequency of alloreactive T cells activated by this pathway is several logs higher than those that can be activated by indirect allorecognition alone. The vigor of the initial episode of acute rejection after organ transplantation has been classically attributed to donor-derived hematopoietic antigen presenting cells, which migrate from the transplanted organ to the host's peripheral lymphoid tissue and activate T lymphocytes by the direct pathway of allorecognition. As these passenger leucocytes survive only briefly after migration to the host lymphoid system, allorecognition at later points and subsequential chronic rejection has been attributed to the weaker "indirect pathway".

The present inventors have investigated the role of allograft parenchymal cells in direct allorecognition. (Kreisel, D., et al., A simple method for culturing mouse vascular endothelium, J. of Immunological Methods, 254: 31-45 (2001); Krupnick, et al., Multiparameter flow cytometric approach for simultaneous evaluation of T lymphocyte-endothelial cell interactions, Cytometry (Communications in Clinical Cytometry) 46: 271-280 (2001)). It has been found that even in the absence of professional donor-derived hematopoietic antigen presenting cells, donor parenchymal cells, most likely vascular endothelial cells, can initiate direct alloantigen presentation to alloreactive host T lymphocytes. In fact, the presence of donor derived hematopoietic antigen presenting cells does not affect the tempo of CD8+T cell mediated allograft rejection which can be mediated entirely by parenchymal cells (Kreisel D, Krupnick A S, Gelman A E, Engels F H, Popma S H, Krasinskas A M, Balsara K R, Szeto W Y, Turka L A, Rosengard B R (2002), Non-hematopoietic allograft cells directly activate CD8+ T cells and trigger acute rejection: an alternative mechanism of allorecognition, Nature Medicine 8:233-239). Thus, a cell population that resides permanently in the transplanted organ and plays a critical role in organ function also can initiate a powerful pathway of antigen presentation leading to chronic rejection and organ destruction. This new paradigm of allorecognition presents yet another major barrier to successful, long-term, solid organ transplantation. These results call into question whether whole organ replacement is truly necessary for treatment of end stage heart failure. Since the majority of heart failure patients suffer a decline in function due to deleterious ventricular remodeling resulting from a limited size infarction, heart failure may be prevented by restoring contractility solely in this portion of the myocardium.

These issues have led the present inventors to reexamine the necessity of whole organ transplantation and to investigate the possibility that replacement of only the portion of myocardium lost to ischemic insult or congenital malformation might suffice in treating cardiac dysfunction. Despite long-standing assumptions that adult myocardium can not regenerate and lacks stem cells to support such regeneration, recent experimental data has shown that adult and fetal stem cells can differentiate into cardiac myocytes, repopulate myocardial scar, and improve myocardial function. Based on these findings experimental efforts have become focused on the establishment of small animal models of adult and congenital cardiac disorders in order to develop novel cell delivery strategies such as cellular cardiomyoplasty, and myocardial tissue engineering, as well as to harness the innate regenerative capacity of myocardial tissue.

Tissue engineering is a multidisciplinary field combining principles of engineering and biological science and focuses on creating viable organs and tissues to address the limitations of allogeneic solid organ and cell transplantation. The basic principle involves in vivo implantation of a cell-matrix construct in order to replace diseased or deficient tissues with recapitulation of structure after resorption or remodeling of the matrix. Recent developments in successful tissue engineering of cardiac valves and blood vessels have opened up the possibility of reconstructing the hypoplastic left heart by replacing the atretic aortic arch and valve with autologous living constructs that can properly grow during the child's development (Hoerstrup S P, Sodian R, Sperling J S, Vacanti J P, Mayer J E, Jr. (2000), New pulsatile bioreactor for in vitro formation of tissue engineered heart valves. *Tissue Engineering* 6:75-79; Niklason L E, Gao J, Abbott W M, Hirschi K K, Houser S, Marini R, Langer R (1999), Functional arteries grown in vitro. Science 284: 489-493; Shinoka T, Breuer C K, Tanel R E, Zund G, Miura T, Ma P X, Langer R, Vacanti J P, Mayer J E, Jr. (1995), Tissue engineering heart valves: valve leaflet replacement study in a lamb model, *Annals of Thoracic Surgery* 60: S513-516). Complete correction of cardiac anomalies, however, is limited by the inability to engineer functional ventricular tissue and to enlarge the ventricular cavity. Manipulation of the native heart for tissue engineering purposes is possible in a large animal model under complete cardiopulmonary bypass, but no comparable technology has been available for rodent models (Shinoka T, Ma P X, Shum-Tim D, et al., Tissue-engineered heart valves, Autologous valve leaflet replacement study in a lamb model. *Circulation* 1996; 94: II164-168). Cardiac tissue engineering in a murine model has been limited by the difficulty of achieving cardiopulmonary bypass utilizing standard techniques. This is unfortunate as the murine model offers the ideal opportunity to study in vivo myocardial tissue engineering with a substantial amount of in vitro data describing the construction of myocardial tissue already available (Carrier R L, Papadaki M, Rupnick M, Schoen F J, Bursac N, Langer R, Freed L E, Vunjak-Novakovic G (1999), Cardiac tissue engineering: cell seeding, cultivation parameters, and tissue construct characterization. Biotechnology & Bioengineering 64: 580-589; Zimmermann W H, Fink C, Kralisch D, Remmers U, Weil J, Eschenhagen T (2000), Three-dimensional engineered heart tissue from neonatal rat cardiac myocytes. *Biotechnology & Bioengineering* 68: 106-114). A rodent model also offers numerous other advantages such as the availability of inbred syngeneic strains, a defined system of stem cells for transplantation, as well as decreased animal cost (Prockop D J. Marrow stromal cells as stem cells for nonhematopoietic tissues. *Science* 1997; 276: 71-74).

The present inventors have developed a novel small animal model of ventricular tissue engineering utilizing heterotopic heart transplantation. Rat heterotopic heart transplantation offers the ability to operate on an explanted donor organ without the necessity of cardiopulmonary bypass or cardiovascular compromise of the recipient host. By manipulating the microsurgical anastomoses at the time of reimplantation, it is possible to vary the hemodynamic loading of the left ventricle. The present inventors have tested several biocompatible matrices for ventricular replacement, validated the ability to augment ventricular volume in a functioning heart, and provided evidence for myocardial replacement utilizing three-dimensional, stem cell-seeded patches or scaffoldings in accordance with the present invention.

Since seeding stem cells or myoblasts into the compromised ventricle has been shown to improve cardiac function, numerous laboratories have focused on studying cellular cardiomyoplasty as a means of reversing myocardial dysfunction (Sakai T, Li R K, Weisel R D, et al. Autologous heart cell transplantation improves cardiac function after myocardial injury. Annals of Thoracic Surgery 1999; 68: 2074-2080; discussion 2080-2071; Li R K, Jia Z Q, Weisel R D, Merante F, Mickle D A. Smooth muscle cell transplantation into myocardial scar tissue improves heart function, *Journal of Molecular & Cellular Cardiology* 1999, 31: 513-522; Klug M G, Soonpaa M H, Koh G Y, Field L J, Genetically selected cardiomyocytes from differentiating embryonic stem cells form stable intracardiac grafts, *Journal of Clinical Investigation* 1996; 98: 216-224). This technology, however, does not address the absence of myocardium resulting from congenital malformation. The paucity of investigation within this field has been mainly due to the lack of a suitable animal model for the study of ventricular tissue engineering.

The present inventors have provided a model for ventricular tissue engineering that can facilitate studies into the replacement or augmentation of myocardial tissue. By avoiding the need for cardiopulmonary bypass, this model can be utilized in small laboratory animals. By avoiding manipulation and infarction of the native heart excessive animal loss is prevented. Since the described model allows the creation of a fully functioning or an unloaded left ventricle, tissue engineering and remodeling can be studied under normal physiologic conditions or under conditions modeling mechanical circulatory support with a left ventricular assist device.

Composite tissue constructed from biocompatible and biodegradable scaffoldings seeded with single cells or tissue equivalent has been investigated for use in tissue engineering (Shinoka T, Ma P X, Shum-Tim D, et al, Tissue-engineered heart valves, Autologous valve leaflet replacement study in a lamb model, *Circulation* 1996; 94: II164-168; Sakata J, Vacanti C A, Schloo B, Healy G B, Langer R, Vacanti J P, Tracheal composites tissue engineered from chondrocytes, tracheal epithelial cells, and synthetic degradable scaffolding, *Transplantation Proceedings* 1994; 26: 3309-3310; Kaihara S, Vacanti J P, Tissue engineering: Toward new solutions for transplantation and reconstructive surgery, *Archives of Surgery* 1999 134: 1184-1188; Juang J H, Bonner-Weir S, Ogawa Y, Vacanti J P, Weir G C, Outcome of subcutaneous islet transplantation improved by polymer device, *Transplantation* 1996; 61: 1557-1561). Little data, however, is available on the use of such materials for ventricular replacement. The in vitro construction of porous hydrogels with similar characteristics to myocardial extracellular matrix has been previously reported. When cardiac myocytes are cultured within this matrix they organize into a three-dimensional myocardial tissue with physiologic characteristics similar to those of native heart tissue (Zimmermann W H, Fink C, Kralisch D, Remmers U, Weil J, Eschenhagen T, Three-dimensional engineered heart tissue from neonatal rat cardiac myocytes. *Biotechnology & Bioengineering* 2000; 68: 106-114).

However, there remains a need for the in vitro construction and in vivo transplantation of three dimensional tissue. The present inventors demonstrate herein that mesenchymal stem cells, seeded on a three-dimensional matrix, or cell carrier, can engraft and differentiate within the left ventricle of the heart. A delivery vehicle, or patch, for delivering such cells is described herein.

Macroporous scaffoldings fabricated from polymers of lactide (PLLA) and glycolide (PGA) have been studied as an alternative to naturally derived scaffoldings. They break down by simple hydrolysis to natural metabolic products and their highly porous characteristics (95% porosity) allow the delivery and polymerization of the transplanted cells and collagen hydrogel within the interstices of the matrix (Mooney D J, Breuer C K, McNamara K, Vacanti J P, Langer R, Fabricating tubular devices from polymers of lactic and glycolic acid for tissue engineering. Tissue Engineering 1995; 1: 107-118). PGA based scaffoldings have been particularly attractive to the field of tissue engineering due to their rapid rate of degradation and near complete hydrolysis by four weeks in vivo (Peters M C, Mooney D J. Synthetic extracellular matrices for cell transplantation, In: Liu D M, Dixit V, eds., *Materials Science Forum* Vol. 250. Switzerland: Trans Tech Publications, 1997: 43-52). PGA mesh has been successfully used for the delivery of chondrocytes and tracheal epithelial cells for engineering of cartilage; however, its utility for myocardial tissue engineering has not been successfully demonstrated (Sakata J, Vacanti C A, Schloo B, Healy G B, Langer R, Vacanti J P, Tracheal composites tissue engineered from chondrocytes, tracheal epithelial cells, and synthetic degradable scaffolding, *Transplantation Proceedings* 1994; 26: 3309-3310). Studies by the present inventors indicate that the use of this matrix within the heart results in an intense inflammatory response. Since this inflammatory response has limited PGA's ability to serve as a vehicle for cellular transplantation in other organ systems, similar limitations will likely be encountered in the heart.

As will be explained below, the present inventors have successfully demonstrated the use of PLLA matrix for cell transplantation in the heart. Although little degradation of PLLA occurs within the first year, with the potential for infectious complications associated with any foreign body, minimal inflammation was detected by the present inventors in scaffoldings constructed around PLLA matrix.

Consideration of the cell delivery approach for broader based applications is limited by the variety of cells necessary for proper reconstruction of extensive congenital malformations involving several organ systems or anatomic defects requiring a variety of tissues for reconstruction, such as congenital cardiac anomalies. The application of this concept to cardiac tissue engineering has been further complicated by the practical concerns of donor site morbidity and the difficulty of expanding differentiated cardiac myocytes in vitro. These concerns may be overcome by the ability to isolate and expand a population of multilineage stem cells.

Mesenchymal stem cells can be isolated from the bone marrow of numerous species and have been shown under specific circumstances to differentiate into various cell types including osteocytes, chondrocytes, adipocytes, as well as skeletal and cardiac myocytes (Pittenger M F, Mackay A M, Beck S C, et al, Multilineage potential of adult human mesenchymal stem cells, *Science* 1999, 284 (5411): 143; Wakitani S, Saito T, Caplan A I, Myogenic cells derived from rat bone marrow mesenchymal stem cells exposed to 5-azacytidine, *Muscle & Nerve* 1995; 18 (12): 1417; Makino S, Fukuda K, Miyoshi S, et al. Cardiomyocytes can be generated from marrow stromal cells in vitro, *Journal of Clinical Investigation* 1999; 103 (5): 697). The feasibility of isolating such cells and expanding them ex vivo for autologous tissue engineering in the adult has previously been studied (Bruder S P, Kraus K H, Goldberg V M, Kadiyala S., The effect of implants loaded with autologous mesenchymal stem cells on the healing of canine segmental bone defects, *Journal of Bone & Joint Surgery*—American Volume 1998; 80 (7): 985).

As most anatomic defects, including those of the heart, are routinely diagnosed during the first trimester of gestation by prenatal ultrasonography, a recently described concept of perinatal tissue engineering has emerged. This therapeutic strategy involves in utero harvest of fetal tissue, isolation, in vitro expansion, and organization of such autologous cells on a synthetic matrix creating an engineered tissue construct. As all manipulation occurs parallel to ongoing gestation, at birth the infant can benefit from surgical reconstruction utilizing this autologous tissue. To date, this concept has been explored as an experimental therapeutic strategy for reconstruction of muscular diaphragmatic defects, bladder extrophy, as well as superficial skin defects. Due to donor site morbidity and the difficulty of in vitro expansion of differentiated cardiac myocytes, such an approach has not been applied to myocardial tissue engineering. As numerous investigators have described cardiomyocytic differentiation potential of adult bone marrow-derived mesenchymal stem cells, the present inventors hypothesized that the fetal liver, the hematopoietic organ in utero, might contain a similar population of cells. As described below, the present inventors have demonstrated that the fetal liver provides a rich source of mesenchymal stem cells.

The ovine model has been extensively utilized for studies of fetal surgery and perinatal tissue engineering with several established experimental models of human disease including congenital cardiac defects (Fishman N H, Hof R B, Rudolph A M, Heymann M A, Models of congenital heart disease in fetal lambs, *Circulation* 1978; 58 (2): 354). Comparable size of the human and ovine fetus, as well as minimal uterine irritability further increases the utility of this model for fetal studies. The present inventors have demonstrated herein that the ovine fetal liver is a potential source of multilineage mesenchymal stem cells that may be utilized for autologous perinatal tissue engineering, particularly of the heart.

Post-infarction congestive heart failure in adults and congenital heart defects in children remain serious health issues. While cardiac transplantation has been shown to prolong life expectancy, this current form of treatment is limited by lack of suitable organs and chronic rejection. The present inventors have demonstrated the use of engineered constructs to repair damage to the heart, without using whole organ transplantation. It is desirable to provide patches for use in such procedures to repair damage to the heart by, e.g., increasing ventricular volume. It is further desirable to use such patches as cell carriers that may be used to deliver to the heart stem cells for replacement of discrete areas of the myocardium. The present invention addresses these needs in the art.

SUMMARY OF THE INVENTION

The present invention relates to a cell delivery patch for cardiac tissue engineering. According to one embodiment of the invention, an engineered construct such as a patch or cell carrier is provided that may be implanted in the heart of an animal. According to an embodiment of the invention, the patch may be used to enlarge the ventricle of the heart. According to another embodiment of the invention, the engineered patch may be used for the transplantation of cells or tissue into the heart.

In accordance with the invention, a patch for cardiac tissue engineering comprises a gel layer comprising collagen hydrogel supported by an intermediate scaffolding layer comprising biodegradable mesh. This scaffolding layer is, in turn, attached to a reinforcement layer of non-biodegradable support material. The hydrogel of this patch may be seeded with cells or tissue; the cells may be stem cells. The stem cells may be directed to differentiate into cardiac myocytes. This patch may be implanted in the heart to replace discrete areas of the myocardium.

These and other aspects of the present invention will be elucidated in the following detailed description of the invention.

BRIEF DESCRIPTION OF THE DRAWINGS

The application file contains at least one drawing executed in color. Copies of this patent application publication with color drawings will be provided by the Office upon request and payment of the necessary fee.

The present invention will be apparent from the following detailed description of the invention taken in conjunction with the accompanying drawings, of which.

DETAILED DESCRIPTION OF ILLUSTRATIVE EMBODIMENTS

The invention will be described in detail below with reference to FIGS. 1 through 16. Those skilled in the art will appreciate that the description given herein with respect to those figures is for exemplary purposes only and is not intended in any way to limit the scope of the invention. All questions regarding the scope of the invention may be resolved by referring to the appended claims.

As employed above and throughout the disclosure, the following terms, unless otherwise indicated, shall be understood to have the following meanings.

"Anastomosis" refers to an artificially created connection between two structures, organs or spaces.

"Basement membrane" refers to the extracellular matrix characteristically found under epithelial cells.

"Biocompatible" refers to that which is not rejected by the body when placed on or in the body.

"Biodegradable" refers to that which can be chemically degraded via natural effectors, such as, for example, enzymes and other substances found within the body.

"Heterotopic" refers to that which is located away from its normal position.

"Hydrogel" refers to a colloid in which the particles are in the external or dispersion phase and water is in the internal or dispersed phase.

"Mesenchymal" refers to cells or tissue relating to or derived from embryonic tissue derived from mesoderm.

"Mesoderm" refers to the middle of the three germ layers, that arise during development.

"Murine" refers to that which is of or relating to a member of the family Muridae (rats and mice).

"Organoid" refers to that which resembles in superficial appearance or in structure any of the organs or glands of the body.

"Orthotopic" refers to that which is in its the normal or usual position.

"Ovine" refers to that which is relating to, affecting, or derived from a sheep.

"Patch", which may also be referred to as a "scaffolding", refers to a construct, made of one or more types of material, that may be used to repair a defect or damage in an organ, tissue, or region of the body; to deliver biologically active molecules to an organ, tissue, or region of the body; and/or to deliver cells or tissue to an organ, tissue or region of the body. When used for delivery of cells or tissue it may be termed a "cell carrier".

"Slowly biodegradable" refers to that which is not chemically degraded within the body for at least three (3) months.

"Stem cells" refer to relatively undifferentiated cells that are self-renewing and capable of differentiating into one or more cell types.

"Stroma" refers to the matrix or supporting tissue of an organ, as distinguished from its parenchyma or functional element.

"Syngeneic" refers to genetically identical individuals.

Figure 1:
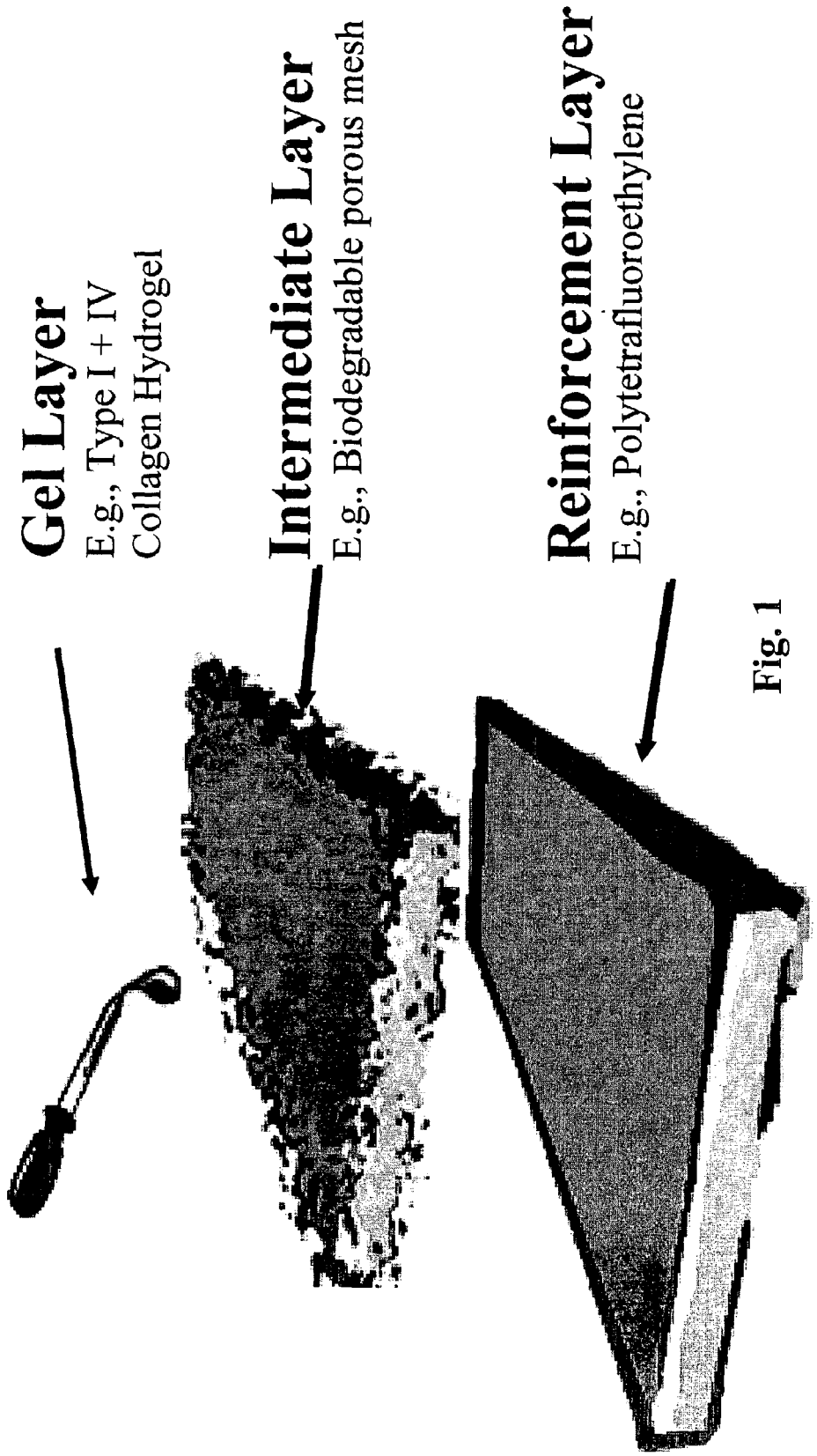
FIG. 1 is a diagram illustrating a patch for cardiac tissue engineering, in accordance with an embodiment of the present invention.

The invention relates to a patch for cardiac tissue engineering, as shown in FIG. 1. According to one embodiment of the invention, the patch comprises a gel layer in contact with an intermediate layer. The intermediate layer is, in turn, attached to a reinforcement layer. In one embodiment of the invention, the gel layer comprises any suitable hydrogel. The hydrogel used preferably has a rubbery, gel-like consistency so that it may be sutured to native myocardium. Preferably, neutralized collagen hydrogel is used. According to one embodiment of the invention, a Matrigel®/Type I collagen hydrogel is used.

In one embodiment of the invention, the intermediate or scaffolding layer comprises porous material that preferably allows for rapid degradation and minimal inflammatory response. Materials that may be used for construction of the intermediate layer include, but are not limited to, co-polymers of glycolic and/or lactic acid. In one embodiment of the invention, the scaffolding comprises porous polylactide biodegradable mesh, as shown in FIG. 2.

In one embodiment of the invention, the reinforcement layer comprises non-biodegradable material, such as, for example, polytetrafluoroethylene (PTFE) (Gore-Tex®, WL Gore & Associates, Inc., Flagstaff, Ariz.), as shown in FIG. 3.

In an embodiment of the invention, a patch for ventricular reconstruction is constructed of Matrigel®/Type I collagen hydrogel supported by a porous polylactide biodegradable mesh and reinforced with polytetrafluoroethylene. Unlike collagen hydrogels constructed without a porous scaffolding, the composite construct may be fashioned into various predetermined organoid shapes and provides optimal handling characteristics necessary for suture placement into ventricular myocardium. Unlike several biodegradable materials evaluated, Gore-Tex® reinforcement prevents distortion of ventricular geometry and aneurysmal dilatation of the functioning left ventricle.

In one embodiment of the invention, biologically active molecules, including, but not limited to, chemokines and cytokines, may be included on or in the patch. Such substances may be included, for example, on or in the gel layer of the patch. In an embodiment of the invention, the patch may be used to deliver biologically active molecules to the heart.

Figure 13:
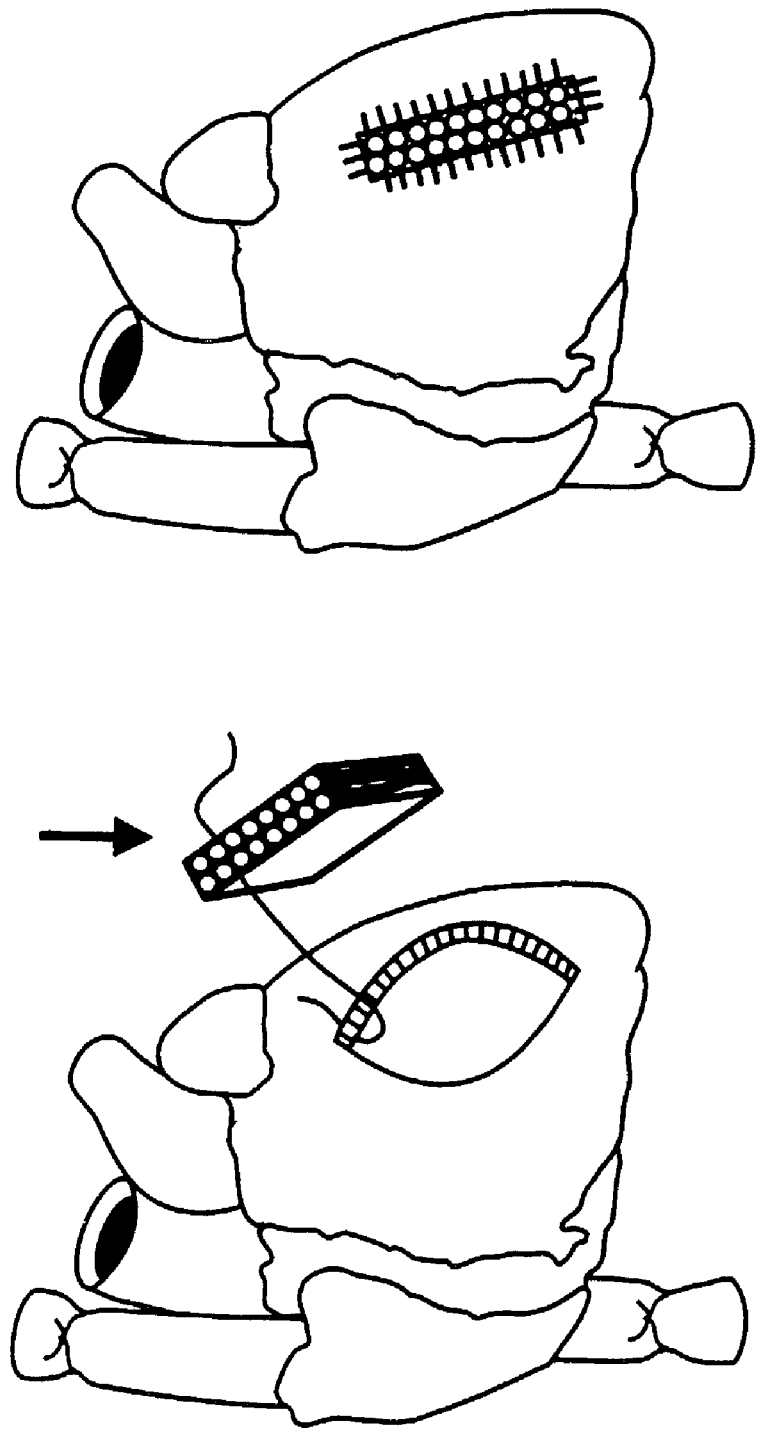
FIG. 13 is a diagram illustrating a cell carrier and method for cardiac tissue engineering, in accordance with an embodiment of the present invention.

In another embodiment of the invention, cells or tissue may be included on or in the patch, forming a cell carrier, as shown in FIG. 13. For example, stem cells may be placed on or in the gel layer of the carrier. These cells preferably differentiate such that they express characteristics of cardiac myocytes. It may be readily appreciated that biologically active agents may be added to the gel layer to enable cells to grow and/or differentiate.

In one embodiment of the invention, multipotent adult bone marrow-derived mesenchymal stem cells are placed on or in the hydrogel of the carrier prior to transplantation. Preferably, these cells express cardiac specific cytoplasmic contractile proteins characteristic of cardiomyocytic differentiation.

In another embodiment of the invention, fetal liver mesenchymal stem cells are included on or in the hydrogel of the carrier prior to transplantation. Preferably, these cells express cardiac specific cytoplasmic contractile proteins suggestive of cardiomyocytic differentiation.

Figure 5B:
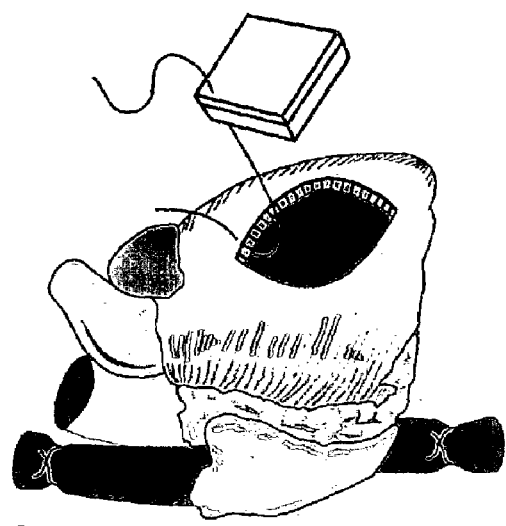
FIG. 5 is a diagram illustrating a patch and method for attachment of the patch to the heart, in accordance with an embodiment of the present invention.
Figure 5C:
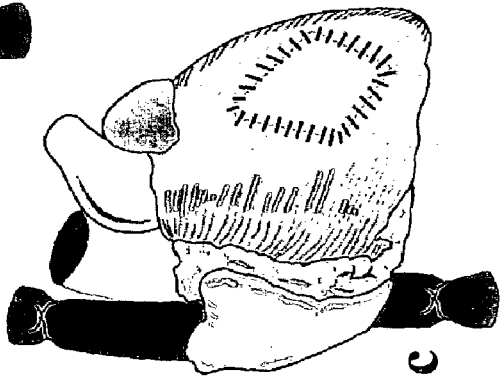

According to an aspect of the invention, the patch of the invention may be implanted in the heart of an animal. In an embodiment of the invention, the size of the ventricular cavity may be augmented by implantation of the patch, as shown in FIG. 5. Preferably, a cell carrier may be used for transplantation of stem cells into the heart, as shown in FIG. 13.

As non-contractile tissue within functioning myocardium undergoes expansion, thinning, and eventual aneurysmal dilatation, biocompatible patches or scaffoldings implanted into this site should withstand such forces in order to prevent ventricular dilatation and distortion of morphology. The present invention avoids this phenomenon by adding a reinforcement layer to the engineered construct. While naturally occurring extracellular matrices, such as bovine and human pericardium, are routinely used in cardiovascular reconstruction and offer the advantage of eventual replacement by native tissue, the present inventors were unable to implement their use as a myocardial scaffolding due to dilatation and aneurysm formation.

Polytetrafluoroethylene is similarly used for soft tissue reconstruction but is not biodegradable, and persists at the site of reconstruction for the life of the repair. Its handling characteristics, however, proved optimal for suture placement into the surrounding myocardium, while its pliancy and elasticity prevented dilatation and aneurysm formation. Although PTFE does present a potential nidus for infection, it has been utilized as a scaffolding for tissue engineering and was successfully implemented using the method of the present invention. The limited elastic properties of PTFE could potentially hinder the contractile function of underlying engineered myocardium, but as minimal fibrosis and adhesion formation occurs to the PTFE matrix, it is expected that this problem could be overcome by simply removing the reinforcement layer at the completion of myocardial regeneration.

As noted above, the patch according to one aspect of the invention may be used as a carrier for cells or tissue. Ventricular reconstruction utilizing fully differentiated cardiac myocytes is hindered by their limited potential for in vitro expansion and donor site morbidity. Mesenchymal stem cells, isolated from bone marrow, present an attractive stem cell source for tissue engineering due to ease of procurement and extraordinary potential for in vitro expansion in the undifferentiated state. It has been suggested that this cell population has cardiomyocytic differentiation potential when injected systemically or into the coronary circulation; therefore, the present inventors have evaluated their utility for tissue engineering of three dimensional myocardial tissue. As described, the present data indicates that marrow stromal cells, transferred within a three-dimensional scaffolding, can engraft and differentiate into muscle with cardiomyocytic potential. Although cytoplasmic contractile protein expression is similar in cardiac and skeletal myocytes, the cardiomyocytic differentiation of the transplanted cells is suggested by the cytoplasmic reactivity of anti-Troponin C (NCL-TROPC), which were found to be reactive only against adult cardiac myocytes. Such patterns of reactivity have been utilized to define cardiomyocytic differentiation of bone marrow stroma. Because bi-nucleation is characteristic of adult rodent cardiomyocytes, this characteristic of the transplanted cells further supports the present model.

As numerous investigators have described cardiomyocytic differentiation potential of adult bone marrow-derived mesenchymal stem cells, the present inventors hypothesized that the fetal liver, the hematopoietic organ in utero, might contain a similar population of cells. To evaluate this possibility, the present inventors modified previously described protocols for the isolation and expansion of adult bone marrow-derived mesenchymal stem cells and applied them to the fetal liver (Pittenger M F, Mackay A M, Beck S C, et al. Multilineage potential of adult human mesenchymal stem cells, *Science* 1999; 284: 143-147). For this set of experiments the inventors chose to work in an ovine model as this animal has been utilized extensively for studies of both fetal surgery and perinatal tissue engineering with numerous established experimental models of human disease such as congenital diaphragmatic hernia, myelomeningocele, abdominal wall defects, as well as congenital cardiac defects. Comparable size of the human and ovine fetus, as well as minimal uterine irritability and low rates of abortion, even after an open hysterotomy, further increase the utility of this animal as a model of fetal surgery.

Tissue was obtained by resecting a segment of the right lobe of the liver in an approximately 100 day gestational fetus (term=145 days). The liver was mechanically degraded, enzymatically digested and separated on a density gradient. Low density cells were collected and enriched for mesenchymal stem cells by plastic adherence. The media was changed at 48 hours to remove non-adherent cells and the adherent cell layer was allowed to expand with bi-weekly media changes. Passage one cells displayed a uniform fibroblast-like morphology, but when exposed to 24 hours of 5-azacytidine or cultured with dexamethasone, this cell population fused into elongated multinucleated cells resembling skeletal muscle. Expression of mRNA for MyoD, a skeletal muscle specific transcription factor was detected by RT-PCR and immunohistochemical evaluation revealed expression of skeletal myosin heavy chain organized in a sarcomeric pattern. The same cells grown in the presence of insulin, dexamethasone, isobutylmethylxanthine, and indomethacin, developed an adipocyte-like morphology exhibiting cytoplasmic lipid droplets intensely staining with Oil-Red-O and if cultured as a pellet micromass in serum free medium, the culture formed lacunae and synthesized a proteoglycan rich extracellular matrix staining with Alcian Blue. If cultured over a bed of type IV collagen and laminin supplemented with growth factors (Matrigel®), spontaneously contracting cells resembling cardiac myocytes could be generated (FIG. 12). More importantly, when organized on a three-dimensional matrix and implanted into the left ventricle of an immunocompromised rat, as described above, cardiomyocytic differentiation was identified by cytoplasmic expression of cardiomyocyte-specific proteins in the transplanted cells (FIG. 16).

As a validation of the clinical assumption that autologous fetal liver can be harvested in utero in a parallel set of studies our colleagues at The Children's Hospital of Philadelphia have been able to perform liver resection on midgestation fetal sheep, similar to methodology utilized herein, with a 75% fetal survival. Thus, the fetal liver may serve as an autologous source of stem cells for myocardial tissue engineering. Ongoing improvements in post-fetal surgery tocolysis and the rapidly expanding development of fetoscopy, including minimally invasive surgical manipulation, offers the potential to minimize mortality after in utero harvest of fetal tissue further, thus making perinatal cardiovascular tissue engineering a clinical possibility.

Spinal dysraphism, congenital diaphragmatic hernia, abdominal wall defects as well as congenital heart defects all represent anatomic anomalies that can be diagnosed early in gestation and require surgical correction either in utero or after birth. Theoretically the immediate availability of autologous tissue for correction of congenital defects upon birth can circumvent the need for complex, staged reconstruction or the use of prosthetic material. While such a concept of perinatal tissue engineering has already been successfully applied to experimental models of isolated congenital anomalies using fully differentiated fetal cells, the present inventors are the first to demonstrate the feasibility of multisystem perinatal tissue engineering as well as cardiac tissue engineering by isolating multilineage stem cells from one fetal organ. As these cells appear to have tremendous capacity for expansion, and ample time is available during gestation, the harvest and expansion of an autologous cell source of myogenic, chondrogenic and endothelial cell progenitors for muscular, valvular and vascular engineering, respectively, may be clinically feasible. Although liver resection on midgestation fetal sheep, using open fetal surgical technique is feasible with a 75% fetal survival, such an approach could carry considerable risk for the mother and fetus if applied clinically. A less invasive and morbid approach would involve fetoscopic or ultrasound guided liver biopsy which is currently possible.

Although others have relied on immortalized bone marrow derived mesenchymal stem cell lines in order to study myogenic differentiation, the present inventors have evaluated early passage cells. Immortalized cell lines or primary cell cultures that have undergone large-scale expansion in vitro and can develop genomic instability, acquire neoplastic potential, and decrease telomere length, thus limiting in vivo lifespan. For all these reasons the utility of cells that have undergone numerous population doublings in vitro has been challenged. Proof of multilineage potential of an immortalized cell line is also questionable due to aberrant gene expression, and it has been documented that cell lines derived even from terminally differentiated cells can be induced to undergo multilineage differentiation in vitro. Since a large number of stromal cells can be obtained from a fetal liver resection, enough stem cells may be obtained to rebuild a small vital piece of fetal or neonatal tissue without extensive in vitro expansion.

To avoid prior in vitro differentiation, the present inventors transplanted passage one undifferentiated liver stroma. This was carried out to further demonstrate the in vivo differentiation potential of the cell population utilizing the heterotopic rat heart as a living bioreactor with microenvironmental cues driving differentiation. Myogenic differentiation was evident in a portion of the transplanted cells. The present inventors have demonstrated that fetal liver stromal cells can be utilized for tissue engineering purposes. The efficiency of such a system may be further optimized by the addition of an in vitro step to induce higher levels of differentiation prior to transplantation. Alternatively, the identification of early markers for lineage specific progenitors may allow for the enrichment and transplantation only of selected portions of the cell population, as it is possible that numerous progenitor subsets represent this cell population as a whole.

As the present inventors have utilized a nuclear labeling and detection system for identification of transplanted stem cells, it is possible that the level of engraftment and differentiation has been underestimated due to loss of DNA BrdU upon successive cell division. It is also possible that the transplanted cell population had fused with local cardiac myocytes rather than undergoing true differentiation. Differentiation in vitro has been evaluated, demonstrating that stem cells present in fetal liver stromal cultures could undergo adipogenic, chondrogenic, and myogenic differentiation prior to in vivo transplantation and co-culture with other cells. While not intending to be limited to any single functional model, it is envisioned that the fetal liver contains stem cells capable of multipotent differentiation. Alternatively, the differentiated cells of the present invention could be derived from multiple progenitor populations committed to different fates rather than a single multipotent stem cell. From the pragmatic perspective of tissue engineering, this argument is of minimal importance. In one aspect of the invention, selective expansion and lineage specific differentiation of such stem cells is accomplished after isolation from the patient.

In one aspect of the present invention, protocols for the induction and identification of adipocytes, chondrocytes and skeletal myocytes from stem cells are used, with ovine specific skeletal muscle transcription factor, MyoD and myosin heavy chain utilized to identify skeletal myocytes in vitro. In one aspect of the present invention, spontaneously contracting cells resembling cardiac myocytes were evident in vitro after culture on a layer of Matrigel®. While initially an unexpected finding, the importance of Matrigel® to the differentiation and development of cardiac myocytes has been documented previously, but the exact component or growth factor responsible for such differentiation still remains to be elucidated. To further define that these cultures truly contained cardiac myocytes protocols for evaluation of lineage specific mRNA and protein expression were utilized according to Krupnick A, Kreisel D, Engels F, et al. A novel small animal model of ventricular tissue engineering. *The Journal of Heart & Lung Transplantation* 2002; 21 (2): 233 (hereby incorporated by reference in its entirety) as well as the methods of Orlic D, Kajstura J, Chimenti S, et al. Bone marrow cells regenerate infarcted myocardium. *Nature* 2001; 410 (6829): 701; Toma C, Pittenger M F, Cahill K S, Byrne B J, Kessler P D. Human mesenchymal stem cells differentiate to a cardiomyocyte phenotype in the adult murine heart. *Circulation* 2002; 105 (1): 93; Malouf N N, Coleman W B, Grisham J W, et al. Adult-derived stem cells from the liver become myocytes in the heart in vivo. *American Journal of Pathology* 2001; 158 (6): 1929. The lack of commitment to skeletal differentiation in early passage cultures is demonstrated by the absence of Pax 7, thus suggesting that myogenic differentiation does occur from an uncommitted stem cell. Cells with contractile capacity, even committed adult skeletal myoblasts, have been successfully utilized for cardiac tissue engineering. In one aspect of the present invention, the liver-derived cells described above may be utilized for myocardial tissue engineering.

While previous investigators have reported complete lineage specific differentiation utilizing in vitro induction protocols, the present inventors witnessed a somewhat promiscuous expression of a wide variety of phenotypes under numerous induction conditions. Elongated, multinucleated skeletal myocytes and adipocytes, for example, were evident in several culture conditions, albeit at a much lower frequency than that seen after treatment with 5-Aza or adipogenic induction medium respectively. While the inventors noted spontaneously contracting cardiac myocytes only after culture on a layer of Matrigel®, previous investigators have established that cardiac differentiation of multipotent cells can be induced by treatment with 5-Aza. To follow up on this finding, the present inventors specifically evaluated and noted upregulation of atrial natriuretic peptide mRNA after treatment with 5-Aza. It is thus likely that cardiomyocyte differentiation does occur under several in vitro conditions but that the presence of a Matrigel® layer either facilitates spontaneous contractions or increases cardiac differentiation to levels visible under light microscopy.

The present inventors have shown that the fetal liver contains mesenchymal stem cells with multilineage differentiation potential. This work broadens the application of perinatal tissue engineering as a therapeutic alternative for the treatment of a wide variety of congenital anomalies.

Figure 4:
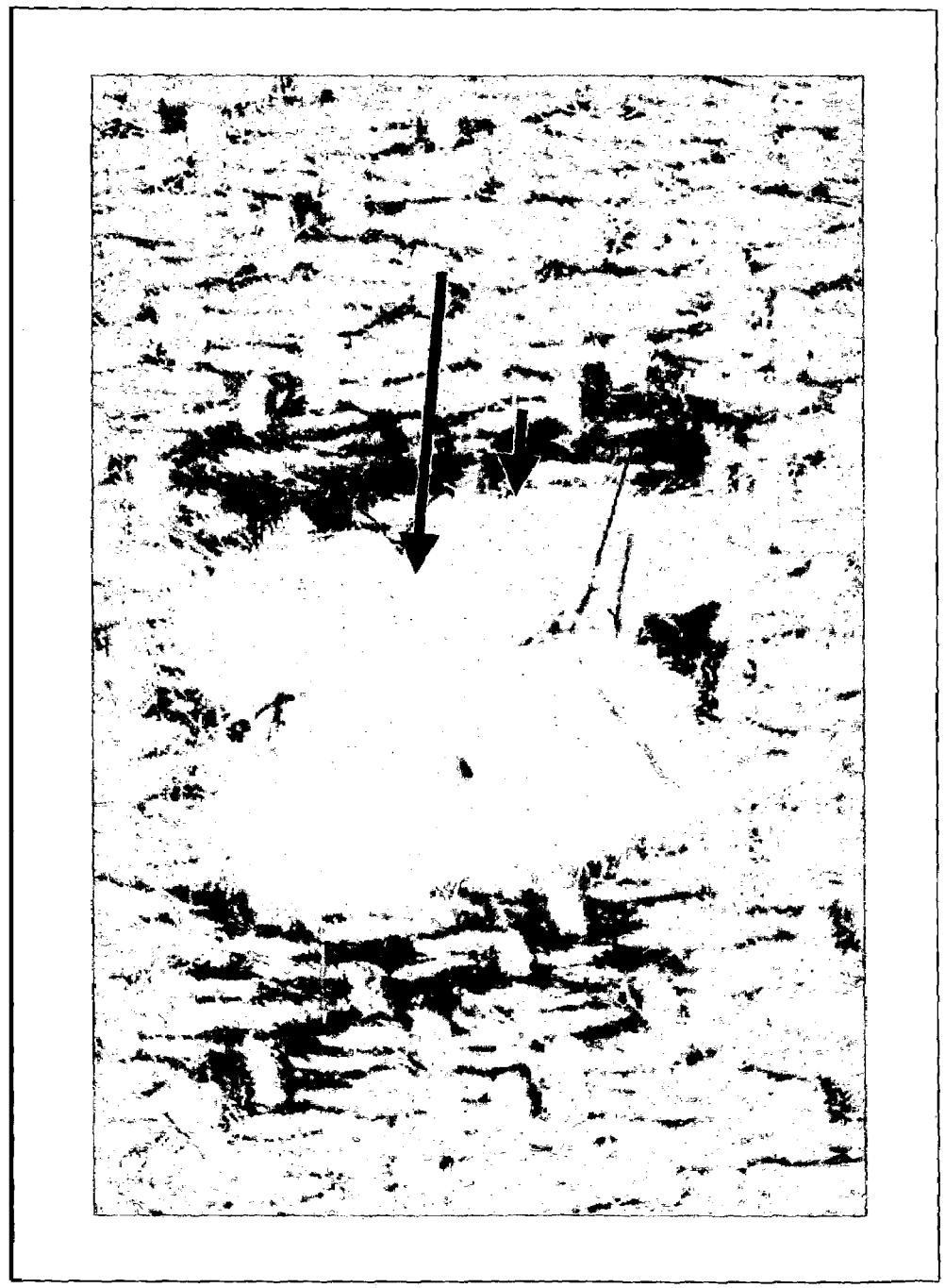
FIG. 4 is a graphic representation of a patch for cardiac tissue engineering, in accordance with an embodiment of the present invention.

A patch according to an aspect of the invention may be transplanted into a recipient heart. According to one embodiment of the invention, the patch is constructed from polytetrafluoroethylene (arrow) secured to PLLA mesh (arrowhead) with 8-0 nylon suture (FIG. 4). This patch was utilized for both ventricular enlargement and stem cell transplantation.

According to an aspect of the invention, the patch may be implanted in a recipient heart to for, example, increase ventricular volume and/or to deliver cells or tissue, such as, for example, stem cells. FIG. 5 shows an example of an implantation according to an aspect of the invention. After cold cardioplegia and explantation, a 6-mm long ventriculotomy was created lateral to the left anterior descending artery (a) and a 4 mm×4 mm patch was implanted into the left ventricle (b) in order to enlarge the ventricular cavity (c).

According to one aspect of the invention, cardiac heterotopic transplantation may be used to evaluate patchs and methods relating to cardiac tissue engineering. This method takes advantage of the fact that an explanted heart, after cold cardioplegia, can tolerate several hours of ischemia without a decrease in performance and if transplanted into a syngeneic animal can function for the life of that animal without immunologic rejection.

Figure 7A:
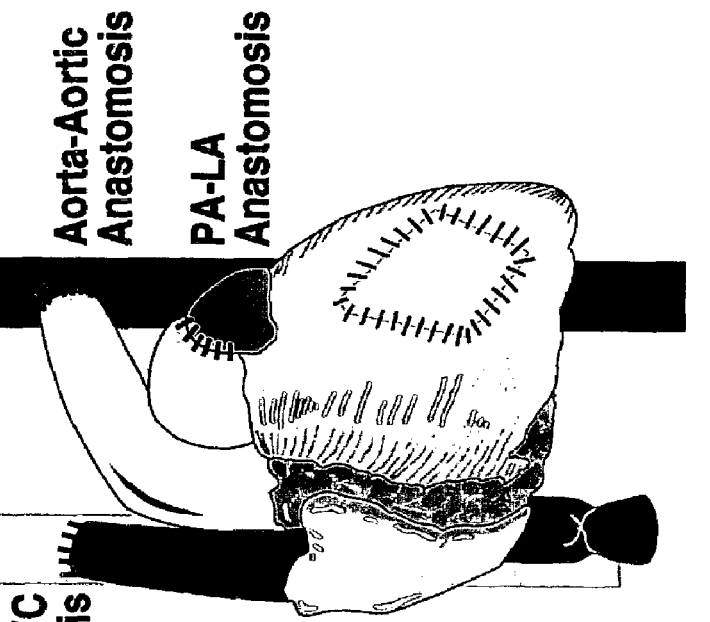
FIG. 7 is a diagram illustrating a patch and method for heterotopic cardiac transplantation, in accordance with an embodiment of the present invention.

One aspect of the present invention relates to a patch and method used to vary the functional capacity of the left ventricle. The microsurgical anastomoses of the transplanted heart were manipulated to create a "heterotopic" heart. In hearts transplanted with a donor to recipient aorto-aortic anastomosis and the donor pulmonary artery to recipient inferior vena caval anastomosis, the left ventricle is functionally excluded from the circulation and models the clinical scenario of left ventricular support provided by a mechanical assist device (FIG. 7a).

Figure 7B:
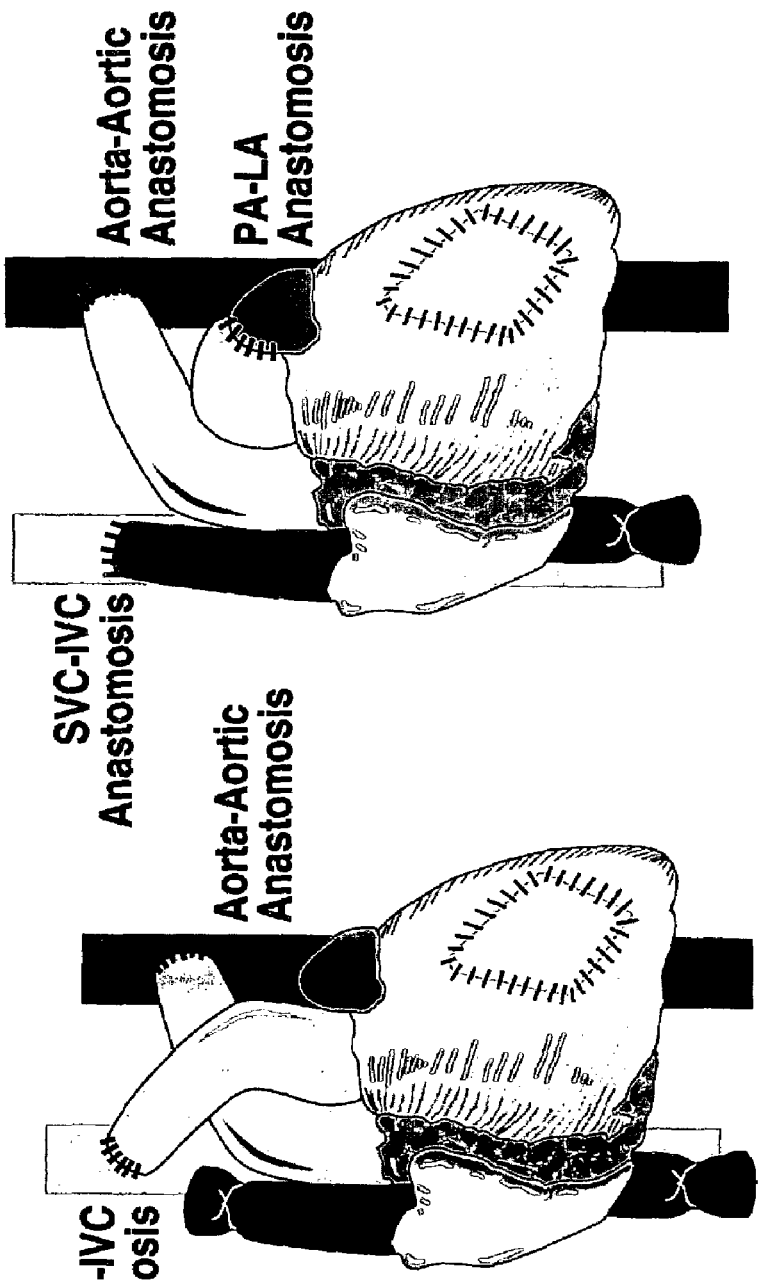

Engineered constructs may be inserted by heterotopic cardiac transplantation producing a volume loaded, functioning left ventricle. When transplanted in a more physiologic fashion, by creating in-flow through a donor superior vena cava to recipient inferior vena cava anastomosis, and loading the left ventricle via a donor pulmonary artery to left atrial anastomosis, the left ventricle is forced to perform mechanical work (FIG. 7b). Unlike the native rat heart, which can generate an ejection fraction close to 65%, ejection fractions of only 20-25% are recorded in this heterotopic heart, as only a small portion of the blood flow is directed into the graft. Despite this limitation, manipulation, infarction and ventricular engineering can be performed on such heterotopic hearts with minimal animal loss. Novel experimental opportunities, which cannot be routinely performed on the rodent orthotopic heart, are feasible in this model.

By studying the fully functioning heart in the heterotopic position, the present inventors were able to evaluate potential augmentation of ventricular volume, thus setting the foundation for reconstruction of ventricular hypoplasia. Both end systolic and end diastolic volumes were enlarged by the implantation of a biocompatible scaffolding. Surprisingly, there was no evidence of ventricular arrhythmia in the experimental group and normal sinus rhythm was restored upon reperfusion and maintained for the duration of the study. Since murine species are relatively resistant to arrhythmia, these results may have been influenced by the choice of this small animal model.

While other studies evaluating ventricular function of the orthotopic heart have expressed stroke volume in ml/kg, relating ventricular function to body weight, the present inventors have estimated ventricular size based on volume alone. Unlike the native heart, it is unlikely that the heterotopic heart grows and remodels in concordance with body weight. Furthermore, since variables such as the width and patency of the hand fashioned anastomosis can affect the ventricular preload, afterload and myocardial growth, relating volume to body weight may not be accurate in the heterotopic heart. By analyzing numerous animals in each group and taking advantage of weight matched, syngeneic rats throughout the study, the present inventors have maximized the ability to control interanimal variability in ventricular size and have assured that ventricular volumes vary solely due to experimental manipulation.

Since the non-ejecting, but contracting left ventricle receives maximum coronary blood flow, the present inventors have optimized the potential for stem cell transplantation by utilizing the non-functioning left ventricle as the model for this portion of the experiment. This version of the model mimics the physiologic status of the left ventricle under complete mechanical circulatory support which not only maximizes blood supply but also minimizes fibrosis, myocyte hypertrophy and potentially allows faster healing and stem cell incorporation. Despite engraftment and myocytic differentiation, contribution of this cell population toward myocardial contractility in the current study is unlikely due to low levels of cardiomyocytic differentiation and no histologic evidence of gap junction formation and electrochemical coupling between the transplanted cells and native myocardium. While this could potentially be due to the limitation of the BrdU detection system, as only cells that have undergone limited division contain detectable BrdU and are identified as originating from the transplanted stroma, the advantages of BrdU labeling, such as lack of reutilization in vivo, create an advantageous system for identification of syngeneic cellular transplants.

According to another aspect of the present invention, a construct may be used to transplant cells or tissue. The present inventors were able to organize and transplant rat bone marrow stroma as a three-dimensional structure. See Example 7. However, the limitation of diffusion and nutrient transfer appeared to hinder cell survival in the center of the engineered constructs. Although neovascularization from the host can be accelerated by incorporation of peptide vascular growth factors or plasmid sequence, engineering three-dimensional tissue around prefabricated vascular networks offer the ultimate potential to overcome mass nutrient transfer.

By developing a patch and cell carrier for cardiac tissue engineering, the present inventors have provided an approach to the correction of complex congenital anomalies in humans. The described approach, however, is not limited solely to childhood disorders. Coronary artery disease and loss of myocardium due to coronary occlusion and ischemic injury is the number one adult cause of death in the developed world. While current surgical therapy, even after infarction, focuses only on the replacement of diseased vessels, the potential to replace myocardial scar with viable engineered myocardium offers a novel therapeutic possibility to treat ischemic myopathy in adults.

EXAMPLES

Example 1

Construction of Biocompatible Scaffolding for Ventricular Replacement

FIG. 1 depicts a patch and a method of making same according to one aspect of the invention.

Collagen hydrogels may be utilized as the basis for ventricular reconstruction of the present invention. Such collagen hydrogels have been investigated for the formation of three dimensional cardiac tissue in vitro (Zimmermann W H, Fink C, Kralisch D, Remmers U, Weil J, Eschenhagen T. Three-dimensional engineered heart tissue from neonatal rat cardiac myocytes. *Biotechnology & Bioengineering* 2000; 68: 106-114). The liquid hydrogel was made by combining 66 µl of type I rat tail collagen (4.6 mg/ml)(BD Biosciences, Bedford, Mass.) with 66 µl of 2× Dulbecco's Modified Eagle's Medium (supplemented with 20% horse serum, 200 µg/ml streptomycin and 200 U/ml penicillin G), 9 µl of 0.1 M NaOH, 25 µl of Matrigel® basement membrane matrix (growth factor reduced, phenol red free) (Collaborative Biomedical, Bedford, Mass.) and 74 µl of 1× Dulbecco's Modified Eagle's Medium (supplemented with 10% horse serum, 100 µg/ml streptomycin and 100 U/ml penicillin G). This mixture was poured into a mold containing a 4 mm×4 mm×2 mm biodegradable scaffolding composed of either polyglycolide (PGA)(2 mm thick, 65 mg/cc fiber density) based or polylactide (PLLA) (2 mm thick, 120 mg/cc fiber density) based porous non-woven mesh (Transome Inc., Palm Bay, Fla.) and allowed to gel at 37° C. prior to further manipulation. In order to facilitate implantation of the constructed scaffolding into the myocardium, the scaffolding was attached to an identically sized reinforcement layer composed of either a biodegradable material such as bovine pericardium (Per-Guard®, glutaraldehyde crosslinked collagen) (Bio-Vascular, Inc., St. Paul, Minn.), an uncrosslinked collagen matrix derived from the human skin (Alloderm, Lifecell, Branchburg, N.J.), or human pericardium (Tutoplast® Processed Pericardium, Biodynamics International, Parsippany, N.J.). A non-biodegradable, synthetic Gore-Tex® polytetrafluoroethylene Soft Tissue Patch (W.L. Gore & Associates, Inc., Flagstaff, Ariz.) was also evaluated as a reinforcement layer. By securing this layer to the epicardial surface, direct apposition of the collagen hydrogel to the myocardial muscle was possible.

Evaluation of Biocompatible Scaffoldings

Figures 2A, 2B:
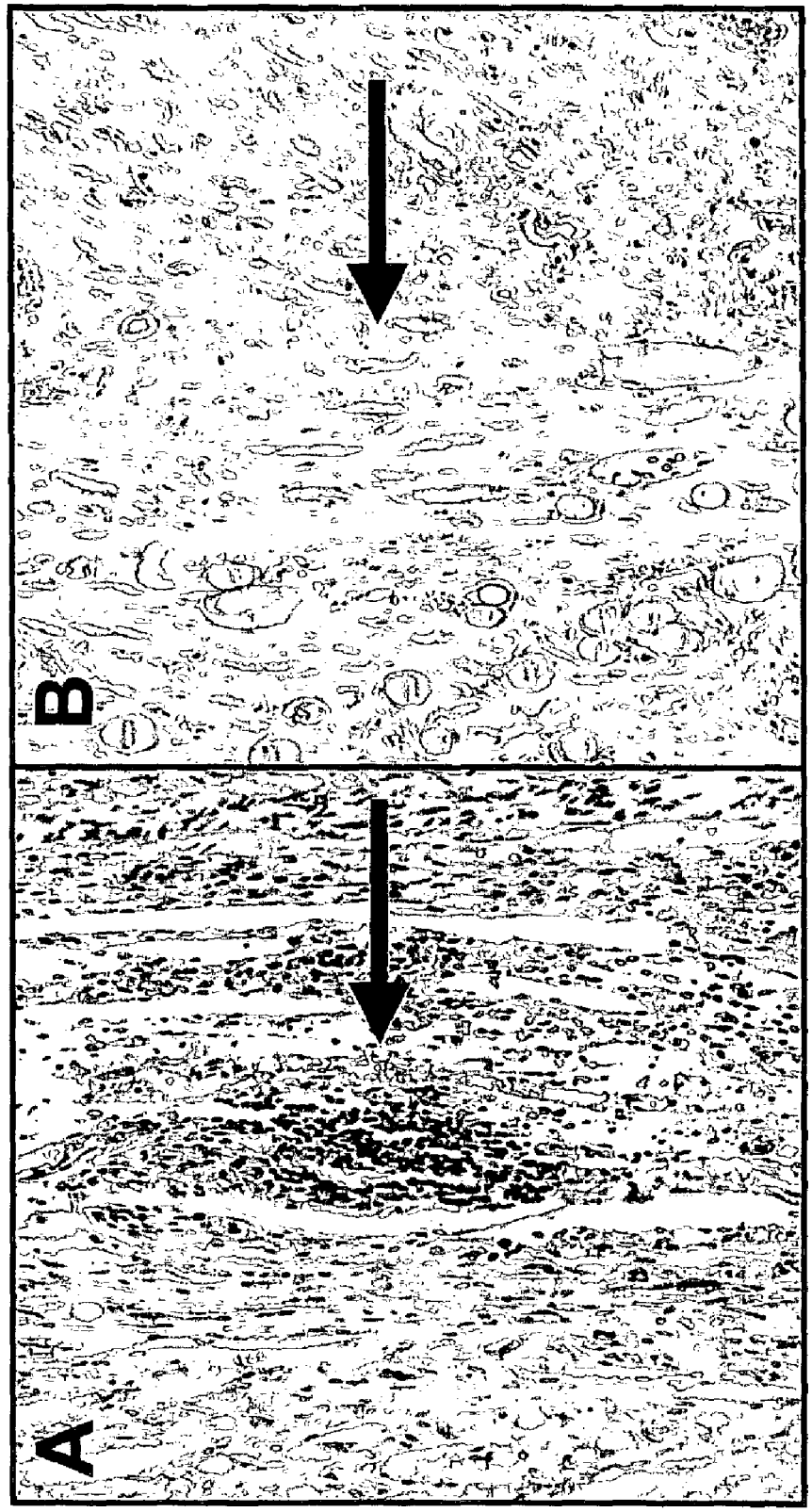
FIG. 2 is a histologic evaluation of materials used to construct the intermediate layer of a patch for cardiac tissue engineering, in accordance with an embodiment of the present invention.

Scaffolding implantation and heterotopic transplantation was accomplished with minimal technical failure after an initial learning curve. Histologic evaluation revealed a high grade inflammatory response in the constructs built around PGA mesh including a dense lymphocytic infiltrate and evidence of chronic inflammation with granuloma formation. (FIG. 2a). No visible inflammation was elicited by PLLA mesh with neovascularization and incorporation of the matrix into the surrounding myocardium (FIG. 2b). Arrows indicate the junction of native myocardium with the engineered construct including remnants of remaining PLLA and PGA (200× magnification (200×), staining with hematoxylin and eosin (H&E)).

Figures 3A, 3B:
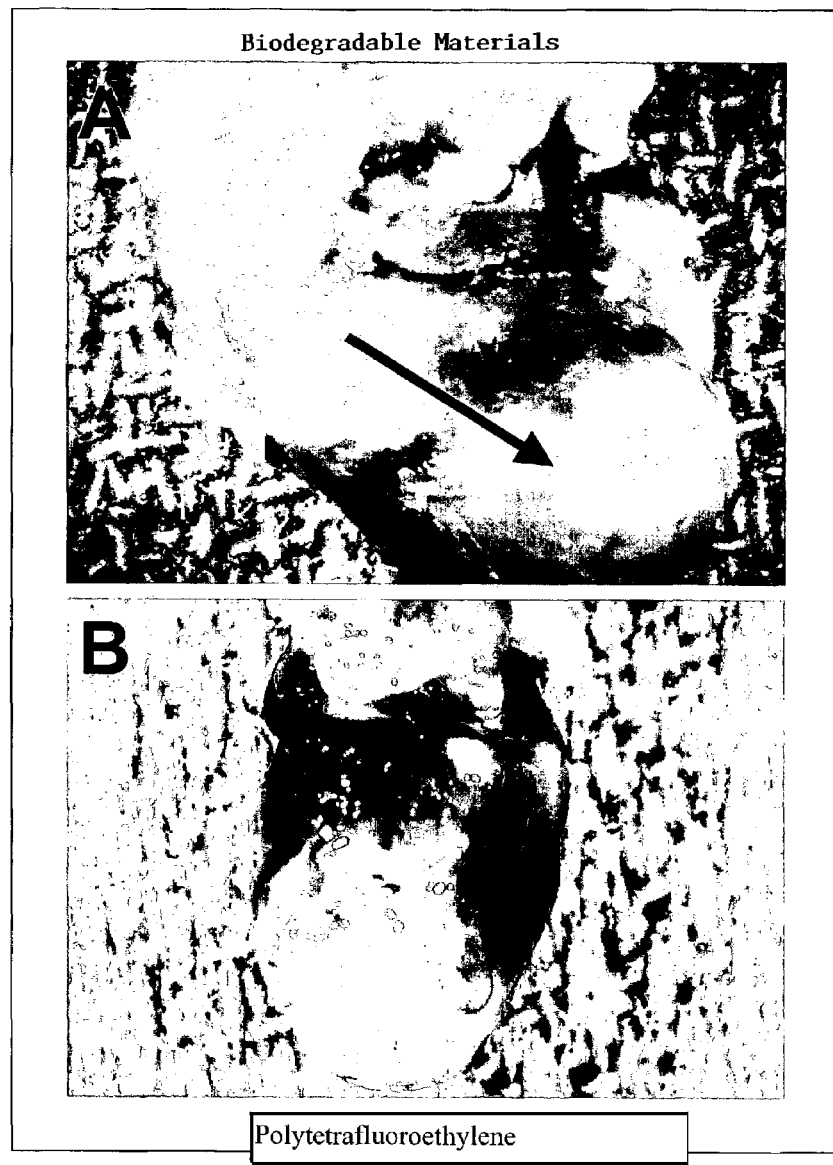
FIG. 3 is a graphic representation of the evaluation of materials used to construct the reinforcement layer of a patch for cardiac tissue engineering, in accordance with an embodiment of the present invention.

Visual inspection one month after transplantation revealed aneurysmal dilatation of all scaffoldings reinforced with biodegradable materials, such as bovine or human pericardium as well as human dermal matrix, when implanted into a functioning left ventricle. FIG. 3a demonstrates that scaffolding reinforced with biodegradable material such as human pericardium showed aneurismal dilatation (arrow) after one month when implanted in a fully loaded ventricle. No aneurysmal dilatation was evident in the scaffoldings reinforced with Gore-Tex® (polytetrafluoroethylene) (FIG. 3b).

Based on these results the rest of the study was conducted utilizing scaffoldings constructed from PLLA mesh and reinforced with Gore-Tex® (FIG. 4).

Example 2

Donor Operation and Scaffolding Implantation

For all except liver cell studies, animals utilized for transplantation consisted of male Lewis (LEW/SsHsd) rats weighing 200-225 g at the time of experimentation (Harlan, Indianapolis, In). All experimental protocols were reviewed and approved by the Institutional Animal Care and Use Committee of The University of Pennsylvania, and followed guidelines set forth in the National Institutes of Health Guide for the Care and Use of Laboratory Animals. Techniques to obtain the donor heart were used as described (Asfour B, Hare J M, Kohl T, et al. A simple new model of physiologically working heterotopic rat heart transplantation provides hemodynamic performance equivalent to that of an orthotopic heart, *Journal of Heart & Lung Transplantation* 1999; 18: 927-936). After induction of anesthesia with enflurane, a midline sternotomy was performed and extended caudally to an abdominal incision, exposing the inferior vena cava (IVC)

and aorta. The animal was heparinized with 300 I.U. of heparin through the IVC and exsanguinated through the abdominal aorta and IVC. Combined retrograde and antegrade cardioplegia was performed sequentially with 3 cc of 4° C. cardioplegic solution injected through the thoracic inferior vena cava and the aortic root via the brachiocephalic trunk. The heart was then harvested by four separate ligatures tying off the distal superior vena cava (SVC), the IVC, the right and left lungs including the left SVC. The great arteries were divided after dissecting off the thymus. The donor heart was kept on ice after explantation and all benchtop manipulation was performed in iced cardioplegic solution.

Figure 5A:
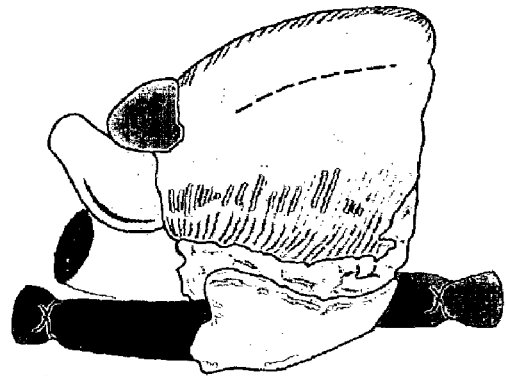
Figure 6:
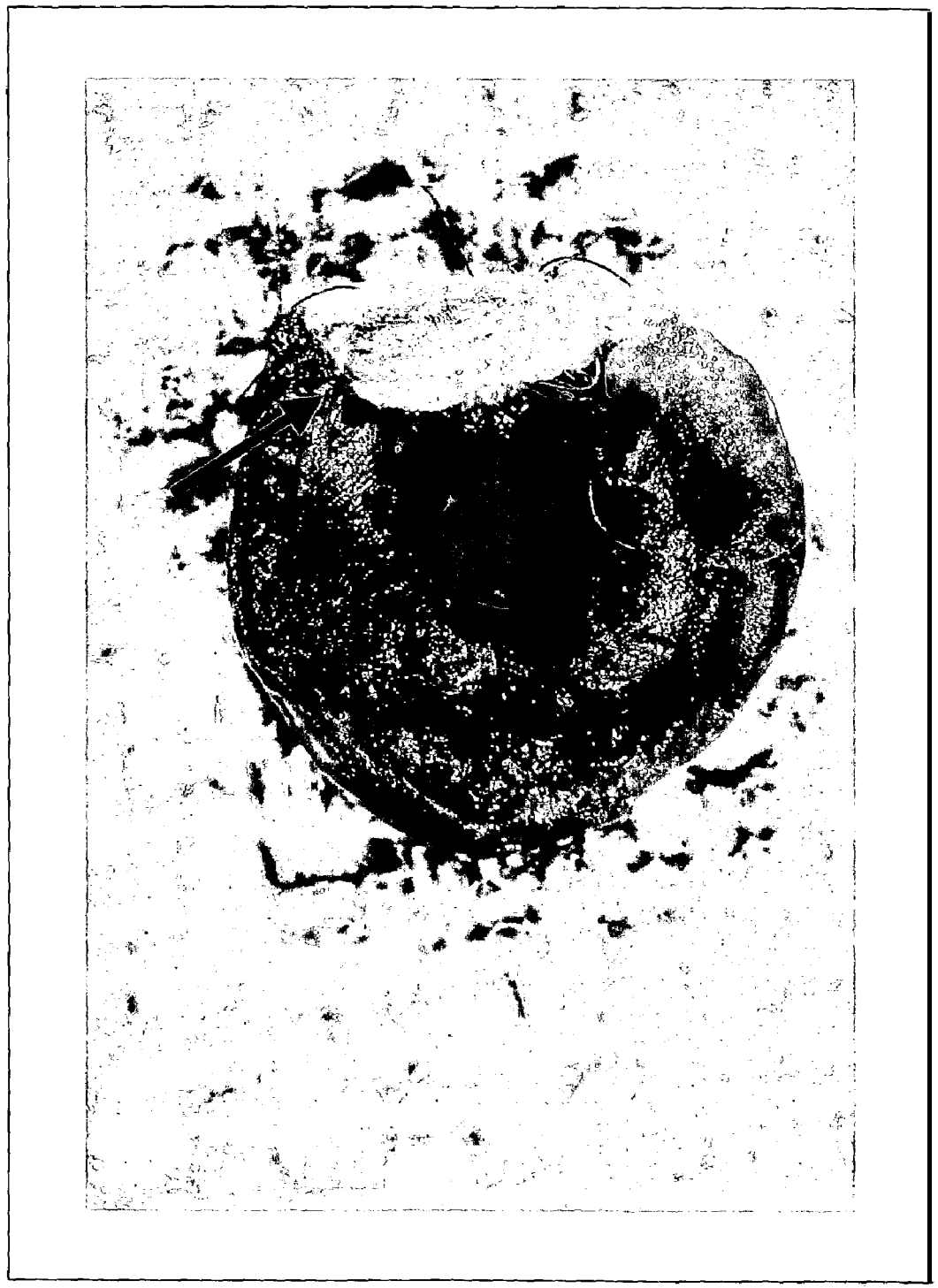
FIG. 6 is a graphic representation of a patch and method for attachment of the patch to the heart, in accordance with an embodiment of the present invention.

Major cardiac vasculature was left undisturbed and a 6-mm long ventriculotomy was created lateral to the left anterior descending artery. A 4 mm×4 mm scaffolding was then implanted into the left ventricle in order to enlarge the ventricular cavity (FIG. 5a,b,c). The reinforcement layer of the scaffolding was sutured to the surrounding epicardial surface of the heart with a running 8-0 nylon suture (US Surgical Corporation, Norwalk, Conn.), allowing direct approximation of the hydrogel impregnated mesh to the adjacent myocardium (FIG. 6) (arrow).

Heterotopic Transplantation

FIG. 7 illustrates heterotopic transplantation techniques used to test patches.

Heterotopic infrarenal abdominal implantation of the graft was performed in a portion of the animals by the technique of Ono and Lindsay, creating a non-functioning left ventricle (Ono K, Lindsey E S. Improved technique of heart transplantation in rats, *Journal of Thoracic & Cardiovascular Surgery* 1969; 57: 225-229). By anastomosing the donor to the recipient aorta and donor pulmonary artery to the recipient inferior vena cava (IVC), a non-functioning left ventricle is created with no intracavitary filling or ejection (FIG. 7(a)).

A volume loaded, functioning left ventricle can be created by anastomosing the donor pulmonary artery (PA) to the donor left atrium (LA) and then attaching the donor superior vena cava (SVC) to the recipient IVC and donor to recipient aorta in an end to side fashion (FIG. 7(b)). (Asfour B, Hare J M, Kohl T, et al. A simple new model of physiologically working heterotopic rat heart transplantation provides hemodynamic performance equivalent to that of an orthotopic heart, *Journal of Heart & Lung Transplantation* 1999; 18: 927-936). In order to prevent suture line bleeding from the functioning left ventricle upon reperfusion, hemostasis was ensured by applying BioGlue® Surgical Adhesive (CryoLife®, Inc., Kennesaw, Ga.) to the epicardial surface at the myocardial/scaffolding interface. Controls consisted of sex and weight matched animals that underwent heterotopic transplantation under similar conditions, without cardiac manipulation by scaffolding implantation and ventricular expansion. One month after implantation the animals were sacrificed and visual and histologic examination of the transplanted patch was performed.

Evaluation of Ventricular Volumes and Electrocardiography

Only the volume loaded, functioning ventricular model, which has been shown to have the functional characteristics identical to the native heart, was utilized for this portion of the study (Asfour B, Hare J M, Kohl T, et al. A simple new model of physiologically working heterotopic rat heart transplantation provides hemodynamic performance equivalent to that of an orthotopic heart, *Journal of Heart & Lung Transplantation* 1999; 18: 927-936). Under general inhalational anesthesia with enflurane, the rat's abdomen was opened, and the heterotopic heart exposed. Acoustic coupling gel was applied to the epicardial surface and 2D images were obtained using a 12-MHz phased-array transducer (Hewlet Packard, Sonos 5500). Long axis views were obtained making sure that the apex, mitral and aortic valves were visualized and the left ventricular end systolic (ESV) and end diastolic (EDV) volumes were calculated using Simpson's rule (method of disks) (Schiller N B, Shah P M, Crawford M, et al. Recommendations for quantitation of the left ventricle by two-dimensional echocardiography. American society of echocardiography committee on standards, subcommittee on quantitation of two-dimensional echocardiograms, Journal of the American Society of Echocardiography 1989; 2: 358-367). Volumes were compared between the experimental and control groups by t test. A three lead EKG of the heterotopic heart was performed at the completion of echocardiography to evaluate the electrical activity.

Evaluation of Ventricular Volumes and Electrocardiography

Figure 8:
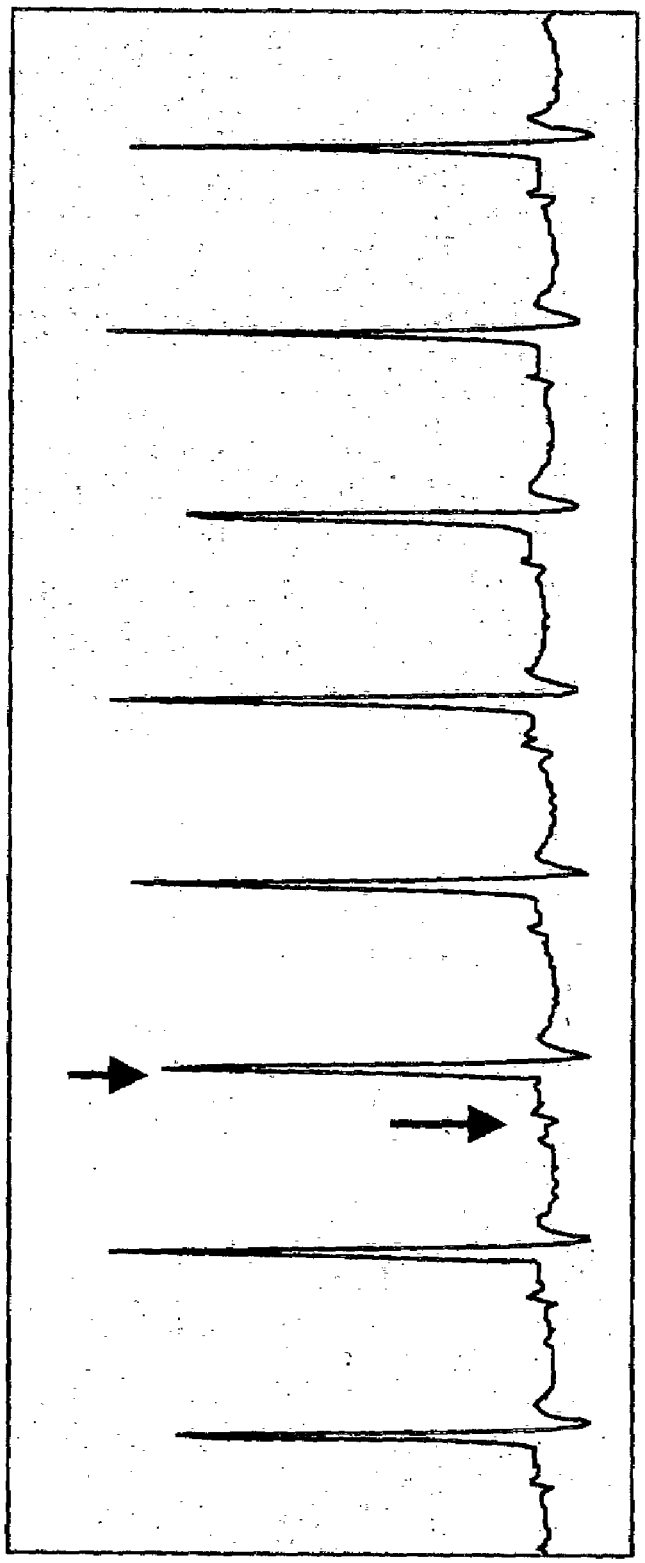
FIG. 8 is a graphical representation of electrocardiography of a heart having an attached patch, in accordance with an embodiment of the present invention.

By incision and construct implantation the present inventors were able to expand the left ventricular volume during systole (ESV=0.26±10.06 cm$^3$) as well as diastole (EDV=0.36±0.07 cm$^3$) over control animals (ESV=0.16±05) and (EDV=0.21±4.05) ($p<0.05$) (Table 1). Echocardiographic examination did not detect any atrial or ventricular arrhythmia, with synchronized contractions and an average heart rate of 260±7 beats/minute (n=3). FIG. 8 documents electrocardiography of the heterotopic hearts after volume augmentation. Electrocardiography of the heterotopic heart failed to detect any arrhythmia, with EKG tracings exhibiting normal sinus rhythm with synchronized contractions, P waves (arrow) and QRS complexes (arrowhead).

Table 1: Comparision of End Systolic and End Diastolic Volumes Between the Experimental and Control Groups

| | End Diastolic Volume | End Systolic Volume |
|---|---|---|
| Experimental Group (Ventricular Expansion) N = 3 | 0.36 ± 0.07 cm$^3$ | 0.26 ± 0.06 cm$^3$ |
| Control Group N = 3 Statistical significance by t test | 0.21 ± 0.05 cm$^3$ P < 0.05 | 0.16 ± 0.05 cm$^3$ P < 0.05 |

By ventricular incision and implantation of a biocompatible patch both end systolic and end diastolic ventricular volumes were expanded. Volumes were calculated from echocardiographic endocardial tracings of heterotopically transplanted hearts one month after implantations.

Example 3

Isolation and Expansion of Mesenchymal Stem Cells

Bone marrow stroma was isolated and enriched for mesenchymal stem cells according to established protocols (Wakitani S, Saito T, Caplan A I. Myogenic cells derived from rat bone marrow mesenchymal stem cells exposed to 5-azacytidine, *Muscle & Nerve* 1995; 18: 1417-1426). Femora and tibiae of male Lewis (LEW/SsHsd) rats weighing 100-150 g were collected and after carefully removing the adherent soft tissue, the bone marrow plugs were flushed out and disaggregated into a single cell suspension by sequential passage through a 22-gauge and 26-gauge needle. This suspension was seeded onto plastic tissue culture plates and maintained in Dulbecco's Modified Eagle's Medium supplemented with 10% fetal calf serum specially selected to support expansion of mesenchymal stem cells (Stem Cell Technologies, Vancouver, Canada) and 1% penicillin/streptomycin. Three days later the medium was changed and the non-adherent cells discarded. Adherent cultures were passaged upon reaching near confluence with 0.25% trypsin in 1 mmol/L sodium ethylenediaminetetraacetic acid (EDTA) (Gibco Laboratories, Grand Island, N.Y.) and split at a ratio of 1:3. Passage two to three cells were used for all experiments. In order to confirm that our cultures contained multipotent cells, a portion of the cultures were subjected to bi-lineage in vitro differentiation according to previously described protocols (Pittenger M F, Mackay A M, Beck S C, et al. Multilineage potential of adult human mesenchymal stem cells, *Science* 1999; 284: 143-147).

Example 4

Harvest, isolation and culture of liver mesenchymal stem cells

After induction of general anesthesia (ketamine 15 mg/kg; 2% Halothane) and maternal and fetal laparotomy in time dated pregnant ewes (Archer Farms, Md.), ranging from 70-110 days gestation (term=145 days), a 2×2×2 cm portion of the right lateral lobe of the fetal and control adult liver was resected for cell isolation. The liver was processed by mechanical and chemical digestion (0.1% collagenase and 33 U/ml dispase)(Sigma-Aldridge, St. Louis, Mo.) and a single cell suspension was then prepared by filtering the solution through a 100 µm filter. The cell suspension was separated over a 1.073 g/ml Percoll solution (Pharmacia, Piscataway, N.J.) at 800 g for 30 minutes and the mononuclear cells collecting at the interface were recovered, resuspended in complete medium consisting of low glucose DMEM (Gibco BRL, Grand Island, N.Y.) supplemented with 10% fetal bovine serum specifically selected to support proliferation of bone marrow derived mesenchymal cells (StemCell Technologies, Vancouver, Ca) and plated at an approximate density of $1.8 \times 10^5$ nucleated cells/cm2 in T175 tissue culture treated flasks (Corning Inc., Corning, N.Y.). After 48 hours the non-adherent cells were removed and upon reaching 50% confluence the adherent cells were harvested and frozen in complete media with 10% DMSO.

Phenotypic Evaluation of Mesenchymal Stem Cells

A portion of the passage one (P1) cells (n=4) were rapidly thawed into tissue culture wells and phenotyped upon reaching 50-80% confluence. A portion of these cells were liberated from the wells with 5 mM EDTA and evaluated for surface protein expression by flow cytometry (FACScan, Becton Dickinson, San Jose, Calif.) while some were left attached to the tissue culture wells and utilized for protein expression by standard immunocytochemical techniques with 3,3'-diaminobenzidine development of the reaction after signal amplification by Vectastain® ABC Avidin:Biotinylated enzyme Complex kit according to manufacturer instructions (Vector Laboratories, Burlingame, Calif.). All antibodies were either specific for ovine antigens or defined as cross-reactivity to ovine proteins prior to staining and appropriate positive and negative controls were utilized throughout the study (Table 2). To confirm the interpretation of immunohistochemistry, a portion of the cultures were simultaneously evaluated for cytoplasmic protein expression by Western blotting utilizing standard cell lysing protocols, separation on a 12.5% SDS-polyacrylamide gel, and visualization by enhanced chemiluminescence (Amersham ECL kit).

Passage one cells were concurrently analyzed for lineage specific mRNA expression. For all reactions, 2 µg RNA was reverse transcribed at 65° C. for 45 minutes and amplified with EZ RTth Taq kit (Perkin Elmer, Conn.) using 300 µM of ovine specific or ovine cross reactive primers as defined by the NCBI data base which included: MyoD sense (5'-GATATGGAGCTGCTGTCGC-3') (SEQ ID NO: 1), MyoD anti-sense (5'-TGCGTTTGCACGCCTTGCAG-3') (SEQ ID NO: 2), ANP (atrial natriuretic peptide) sense (5'-CCGTTTGGAGGACAAGATGCC-3') (SEQ ID NO:3), ANP anti-sense (5'-TCCAATCCTGTCCATCCTTCC-3') (SEQ ID NO: 4), Cardiac troponin T sense (5'-AATGCTGGGCCTGATAAATG-3') (SEQ ID NO: 5), Cardiac troponin T anti-sense (5'-CCGAAACTCGATTCCGTAGA-3') (SEQ ID NO: 6), Pax 7 sense (5'-GAACCTGACCTCCACTGAA-3') (SEQ ID NO: 7), Pax 7 anti-sense (5'-CCTCTGTCAGCTTGGTCCTC-3') (SEQ ID NO: 8), β-actin sense (5'-ATCACCATTGGCAATGAGCGGTTCC-3') (SEQ ID NO:9) and β-actin anti-sense (5'-CTCGTCATACTCCTGCTTGCTGAT-3') (SEQ ID NO:10). Thermocycling was performed on a Hybaid 900 (Hybaid, Middlesex, UK) using the following parameters: 94.5° C. for 120 seconds followed by 34-38 cycles of 95° C. for 30 seconds and 57-61° C. for 150 seconds.

Phenotype of early passage fetal liver stromal cultures

FIG. 10 demonstrates the phenotype of fetal liver stromal cultures.

Figure 10A:
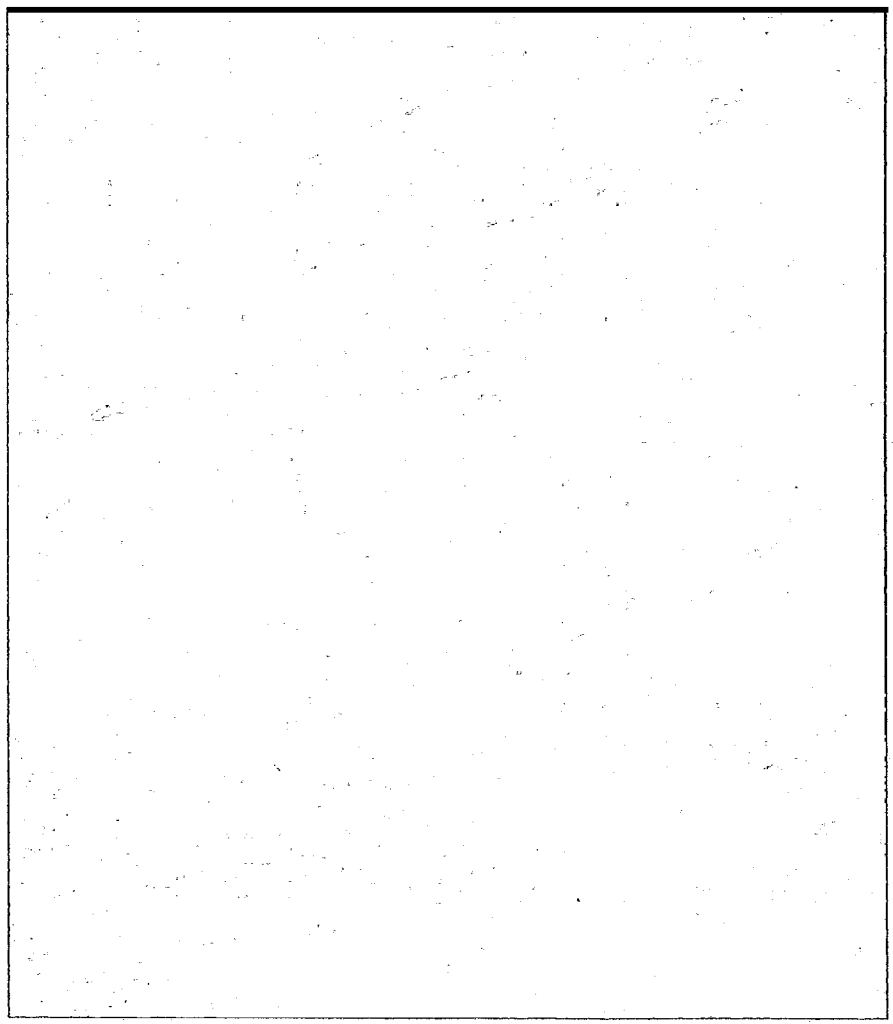
FIG. 10 is a graphical representation of the phenotype of fetal liver stromal cells, in accordance with an embodiment of the present invention.
Figure 10B:
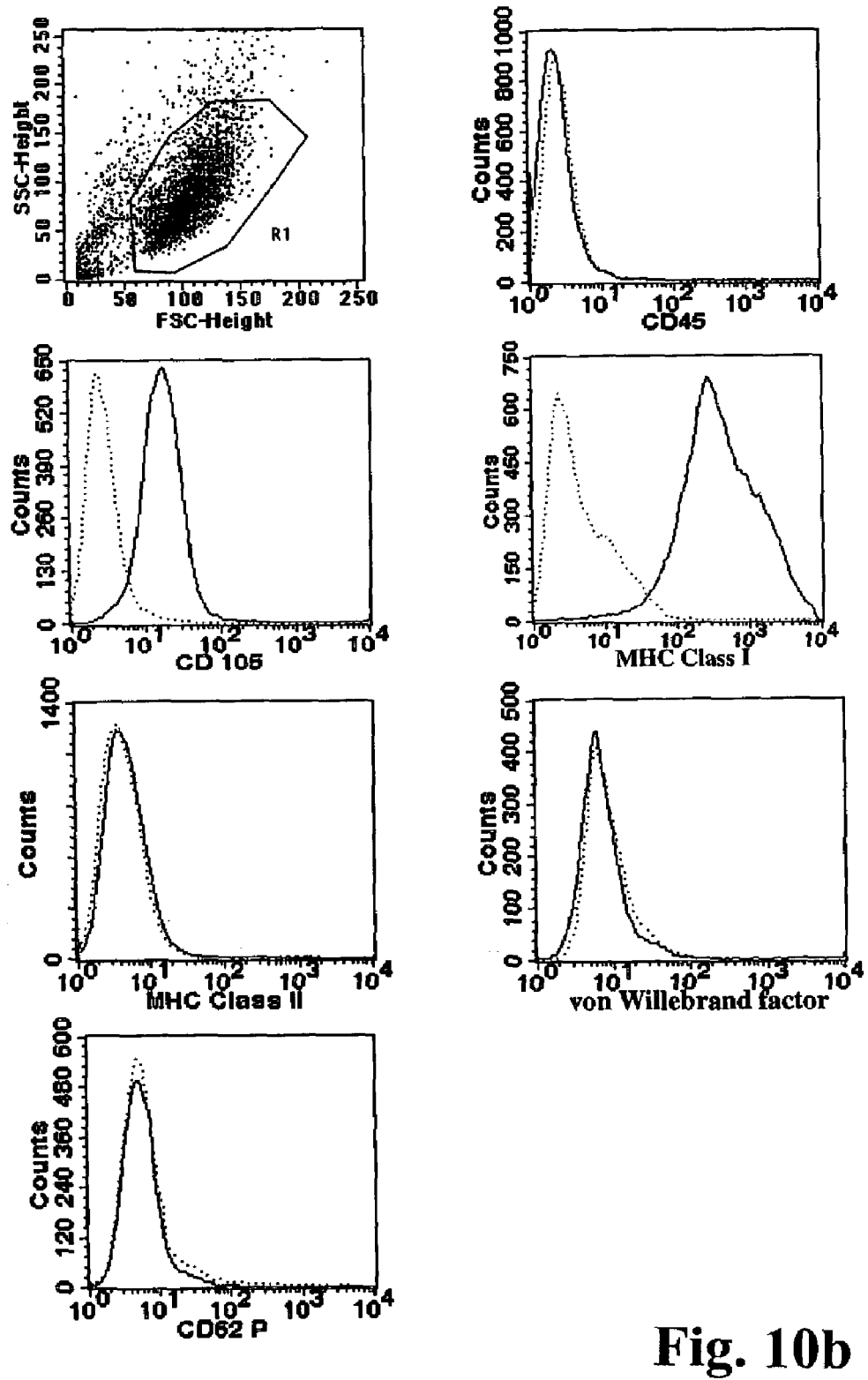
Figure 10C:

Early passage cells had a fibroblast-like appearance upon reaching confluence (200×) (FIG. 10*a*). Flow cytometric analysis revealed a single population of cells by forward and side scatter which was negative for CD45 (common leukocyte antigen) and MHC Class II but positive for both MHC Class I and endoglin (CD 105) (SH2). No fully differentiated endothelial cells were detectable in the early passage cultures based on the lack of expression of von Willebrand factor and P-selectin (CD62P) (solid line represents staining with the purified antibody followed by phycoerythrin conjugated secondary antibody and dotted line is representative of the appropriate purified isotype control followed by phycoerythrin conjugated secondary antibody) (FIG. 10*b*). After two to three weeks of culture in adipogenic media, however, the majority of the cells in the culture developed an adipocyte-like morphology with cytoplasmic lipid droplets staining red by Oil-red-O (FIG. 10*c*). When cultured as a pellet micromass the fetal liver stroma underwent a chondrogenic differentiation with visible lacunae and metachromatic staining by toluidine blue (FIG. 10*d*) while no lacunae were visible in adult liver stromal cells under identical culture conditions (FIG. 10*e*). The presence of cartilage proteoglycans was confirmed by the development of a blue color by Alcian blue staining (FIG. 10*f*) with minimal staining of adult cell cultures (FIG. 10*g*) (200×, inset 400×).

The cultures were negative for CD45 as well as von Willebrand factor and P-selectin confirming lack of hematopoietic and differentiated endothelial cells in the stromal cultures (FIG. 10*b*). Such a phenotype is similar to that previously described for human mesenchymal stem cells (Pittenger M F, Mackay A M, Beck S C, et al. Multilineage potential of adult human mesenchymal stem cells, *Science* 1999; 284 (5411): 143). While immunohistochemical and Western blot analysis did not reveal lineage specific protein expression in the early passage stromal cultures, and all cells were negative for desmin, troponin T, troponin C, a-actinin, MyoDI and MEF2 relative to the appropriate isotype control, the much more sensitive RT-PCR analysis did detect low levels of lineage specific markers such as the skeletal muscle transcription factor MyoD 1 and cardiac muscle specific mRNA for atrial natriuretic peptide and cardiac troponin T (Table 2). Thus, either expression of these proteins is controlled at the translational level, or a very low level of protein translated in early passage cells could not be detected.

TABLE 2

Characterization of Early Passage Fetal Liver Stem Cells

| Antigen/Marker | Reactivity |
|---|---|
| Flow Cytometry | |
| CD 45 (clone VPM18)[1] | − |
| Endoglin (SH2) (clone 266)[2] | + |
| MHC Class I (clone VPM19)[1] | + |
| MHC Class II β chain (DR) (clone VPM37)[1] | − |
| Von Willebrand factor (clone 2F2-A9)[2] | − |
| P-selection (CD 62P) (clone AK4)[2] | − |
| Immunohistochemistry | |
| skeletal myosin heavy chain (clone NOQ7.5.4D)[3] | − |
| α-actinin (clone EA-53)[3] | − |
| Troponin T (clone JLT-12)[3]* | − |
| Troponin C (NCL-TRPC)[4] | − |
| Desmin (NCL-Des-Der II)[4] | − |
| Myo-D (NCL-MyoD1)[4] | − |
| MEF-2 (sc-313)[5] | − |
| RT-PCR | |
| MyoD | + |
| Atrial natriuretic peptide (ANP) | + |
| Cardiac troponin T | + |
| Pax 7 | − |

[1]Serotech LTD., Oxford UK
[2]Parmigen, San Diego, Ca
[3]Sigma Chemical Co., St Louis, MO
[4]Novocastra Laboratories Ltd., Newcastle, UK)
[5]Santa Cruz Biotechnology, Inc.
*confirmed by Western blot

Example 5

In vitro differentiation of liver stem cells utilizing defined media supplementation To assess the differentiation of liver mesenchymal stem cells, defined media supplementation was utilized. Adipogenic differentiation was assessed by culturing P1 liver stromal cells as a monolayer and upon reaching 50-70% confluence treating the cultures with several 72 hour cycles of adipogenic induction medium consisting of $10^{-6}$ M dexamethasone, 0.5 mM methyl-isobutylxanthine, 10 µg/ml of bovine insulin, 100 mM indomethacin (all from Sigma Chemical Co., St. Louis Mo.) and 10% FBS in low glucose DMEM (Pittenger M F, Mackay A M, Beck S C, et al. Multilineage potential of adult human mesenchymal stem cells. *Science* 1999; 284 (5411): 143.). Chondrogenesis was accomplished by culturing the cells as a micromass pellet in the presence of a defined serum free medium as described previously by Solchaga L A, Johnstone B, Yoo J U, Goldberg V M, Caplan A I. High variability in rabbit bone marrow-derived mesenchymal cell preparations, *Cell Transplantation* 1999; 8 (5): 511, while multilineage and myogenic differentiation was induced by 24 hour treatment with 10 µM 5-Aza-2'-deoxycytidine (5-Aza) or growth in the presence of $10^{-7}$ M dexamethasone (Sigma-Aldridge, St. Louis, Mo.) (Wakitani S, Saito T, Caplan A I. Myogenic cells derived from rat bone marrow mesenchymal stem cells exposed to 5-azacytidine, *Muscle & Nerve* 1995; 18 (12): 141; Grigoriadis A E, Heersche J N, Aubin J E. Differentiation of muscle, fat, cartilage, and bone from stem cells present in a bone-derived clonal cell population: effect of dexamethasone, *Journal of Cell Biology* 1988; 106 (6): 213). Clonal analysis was performed by isolating single-cell derived colonies in 96-well plates by limiting dilution and inducing multilineage differentiation by the addition of dexamethasone.

Matrix Based Differentiation

Since the extracellular environment has been shown to play a role in both cell migration and differentiation, the inventors evaluated the role of the extracellular matrix in the differentiation of liver stromal cells (Cassell O C, Morrison W A, Messina A, et al. The influence of extracellular matrix on the generation of vascularized, engineered, transplantable tissue. *Annals of the New York Academy of Sciences* 2001; 944: 429; Osses N, Brandan E. ECM is required for skeletal muscle differentiation independently of muscle regulatory factor expression. *American Journal of Physiology—Cell Physiology* 2002; 282 (2): C383). A thick layer of either Matrigel® basement membrane matrix or neutralized rat tail type I collagen (BD Biosciences, Bedford, Mass.) as well as tissue culture plates precoated with either laminin, type IV collagen or fibronectin (BioCoat™ Labware, Bectin Dickinson, Bedford, Mass.) were utilized as a substrate for expansion of P1 cells. The cultures were maintained with media changes every three days for at least 45 days or until visible differentiation was noted.

In vitro differentiation utilizing media supplementation

Liver tissue harvested from a total of 8 fetal lambs was included in this portion of the study with multilineage differentiation detectable in 6 animals. An average of $67.8 \pm 18.5 \times 10^6$ adherent passage one liver stromal cells were obtained from each 8 cm³ piece of fetal liver. After two to three weeks in culture under adipogenic conditions differentiation of adipocytes was noted in the majority (68.4±4.8%) of the adherent cells. Visible change from an elongated to a round morphology was accompanied by the accumulation of Oil-red-O staining lipid-rich vacuoles (FIG. 10c). After a three week culture of identical cells as a pellet micromass in serum-free chondrogenic medium the cultures formed chondrocyte-like lacunae visible as metachromatic purple staining by toluidine blue. The presence of cartilage proteoglycans was confirmed by the development of a blue color on alcian blue staining (FIGS. 10d-g).

Figure 11A:
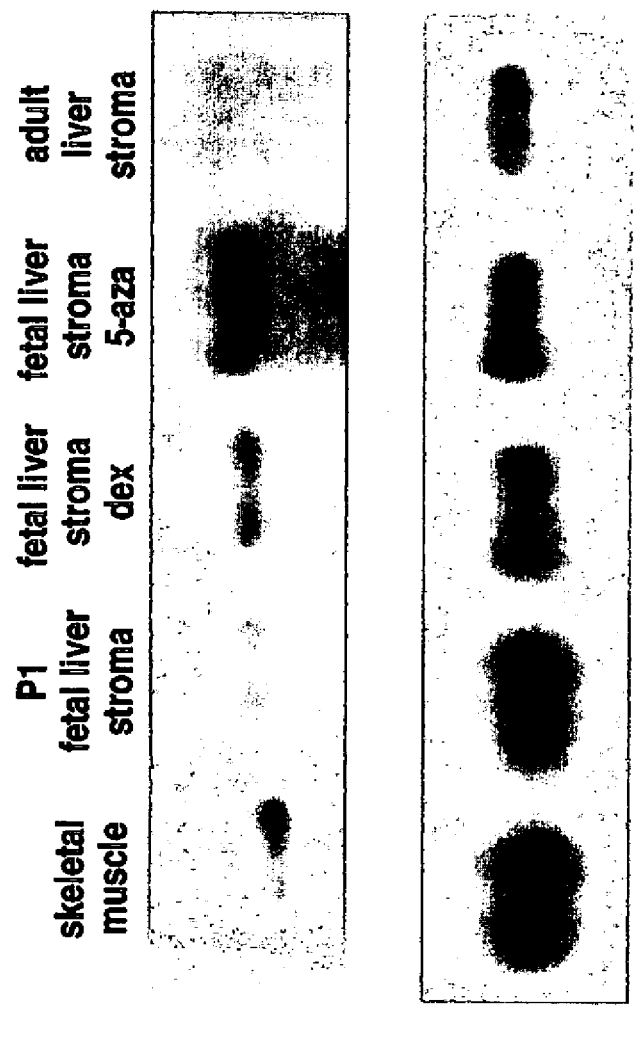
FIG. 11 is a graphical representation of skeletal myogenesis of fetal liver stem cells, in accordance with an embodiment of the present invention.

FIG. 11 demonstrates skeletal myogenesis of fetal liver cells in culture. Upregulation of mRNA for the muscle specific transcription factor MyoD and de novo detection of this transcription factor in the cultures by immunohistochemistry was evident after one month in culture after induction of myogenic differentiation with a 24-hour exposure to 5-aza or the addition of dexamethasone to the cultures (FIG. 11a). The presence of numerous multinucleated cells, resembling developing myotubes, was noted within the cultures and expression of skeletal myosin heavy chain with visible sarcomeric organization confirmed that these cells were indeed skeletal myocytes (FIG. 11b-e). Numerous elongated cells were evident in these cultures (FIG. 11b) and hematoxylin staining revealed the presence of numerous peripheral as well as central nuclei resembling those seen in regenerating skeletal myocytes (FIG. 11c). Immunohistochemical staining revealed the presence of skeletal myosin heavy chain(200×) (FIG. 11d) with visible cross striations suggestive of sarcomeric organization (400×) (FIG. 11e). Contraction leading to tetany could be induced by a one time application of acetylcholine (10 mM).

Figure 11F:
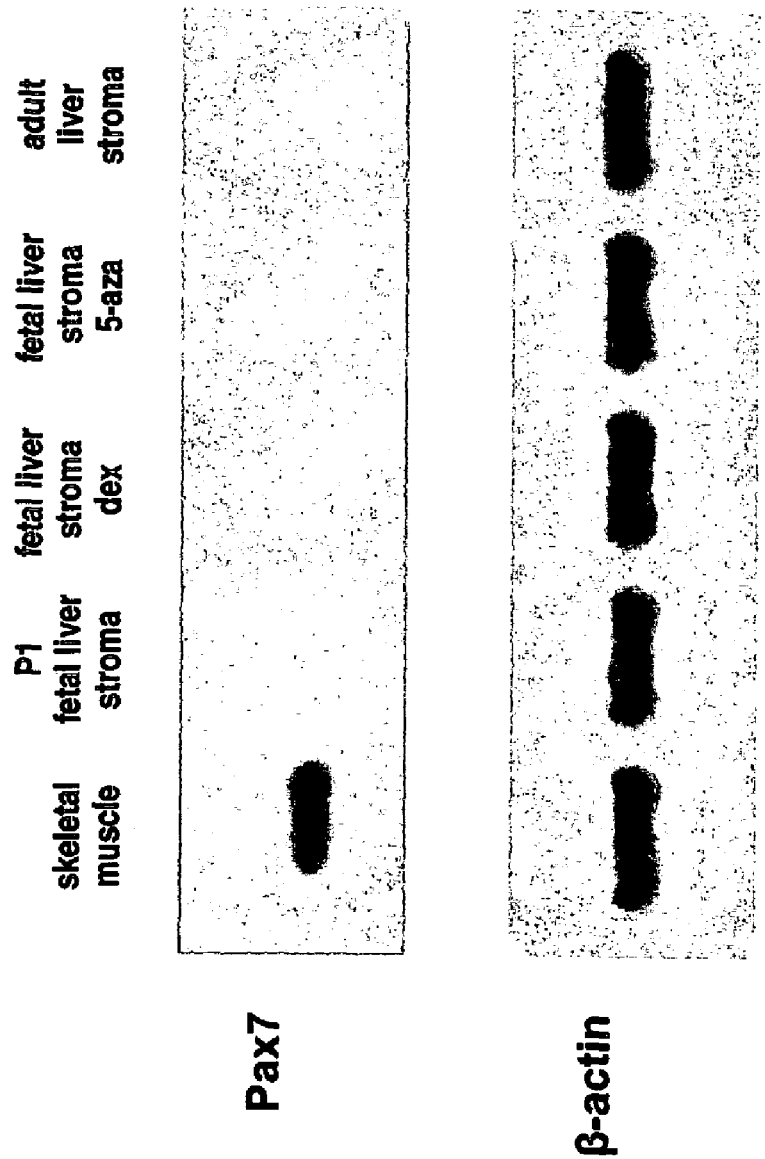

No mRNA for the transcription factor Pax7 was evident during myogenesis in our cultures indicating the lack of satellite or previously committed myogenic cells (FIG. 11f). Under similar differentiation conditions endothelial cells became evident within the stromal cell cultures defined by classic cobble stone-like morphology (FIG. 11g) as well as de-novo expression of von Willebrand factor (FIG. 11h) and p-selectin (data not shown).

Figure 11G:
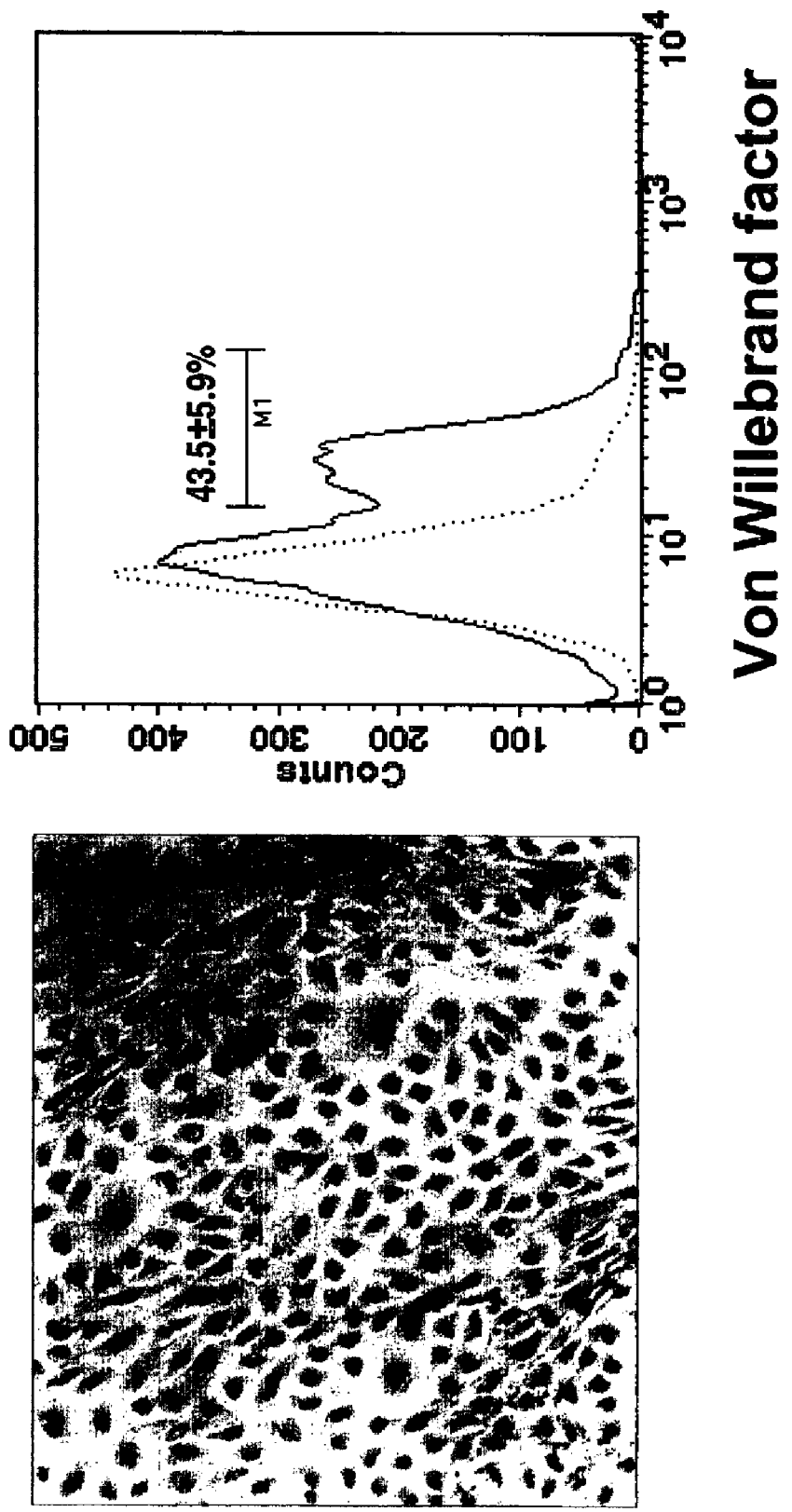

Pax7 is a member of the paired-box family of transcription factors whose expression appears specific to the satellite cells of skeletal myogenic lineage (Seale P, Sabourin L A, Girgis-Gabardo A, Mansouri A, Gruss P, Rudnicki M A. Pax7 is required for the specification of myogenic satellite cells, *Cell* 2000; 102 (6): 77). Interestingly, myogenesis in the cultures proceeds without expression of Pax7, which was not detectable by RT-PCR in early passage undifferentiated stromal cultures or after the formation of myotubes (FIG. 11*f*). These data suggest that no satellite cells or cells restricted to skeletal myogenesis were present in our cultures. This finding also parallels previous observations made for adult pluripotent SP (side population) stem cells where myogenesis proceeds without expression of Pax 7, further strengthening the inventors' conclusion that fetal liver stromal cells contain multilineage progenitors (Seale P, Sabourin L A, Girgis-Gabardo A, Mansouri A, Gruss P, Rudnicki M A. Pax7 is required for the specification of myogenic satellite cells, *Cell* 2000; 102 (6): 77). In addition to skeletal myocytes, some adipocytes were noted under these conditions albeit at lower frequency than under adipogenic conditions (data not shown). Endothelial cells were also noted in the tissue culture wells under these conditions characterized by the classic cobble stone-like morphology. The frequency of endothelial cells was approximately 43.5+5.9% as determined by de novo expression of von Willebrand factor and p-selectin (CD62P) (FIG. 11*g*).

Clonal Analysis

Plating of cells by limiting dilution yielded a total of 19 colonies derived from a single colony forming unit. After exposure to dexamethasone, a non-specific differentiating agent, for 2 weeks, four wells (21%) had evidence of differentiation with the appearance of both elongated multinucleated cells resembling skeletal muscle and round adipocytes with cytoplasmic lipid inclusions. No evidence of differentiation was evident in the other wells.

Matrix Based Differentiation

No morphologic evidence of differentiation was evident after culture of stromal cells on a layer of type I collagen, laminin, type IV collagen, or fibronectin. After three weeks of culture on a layer of Matrigel® basement membrane matrix, however, islands of small spontaneously contracting cells were noted in the fetal liver stroma. The spontaneous contractions were very rapid, automatic and different from those induced by acetylcholine in the differentiated skeletal muscle. The contraction rate varied from approximately 70 to 240 beats per minute. The addition of epinephrine to the tissue culture wells at a final concentration of $10^{-5}$ M resulted in a visible increase in inotropy. Similar to cardiac myocytes derived from embryonic stem cells, the addition of the L-type Ca2+ channel blocker, diltiazem, at a $10^{-4}$ M final concentration, led to a visible decrease in chronotropy with an eventual cessation of spontaneous contractions (Wobus A M., Development of cardiomyocytes expressing cardiac-specific genes, action potentials, and ionic channels during embryonic stem cell-derived cardiogenesis, *Annals of the New York Academy of Sciences* 1995; 752: 460).

Figure 12B:
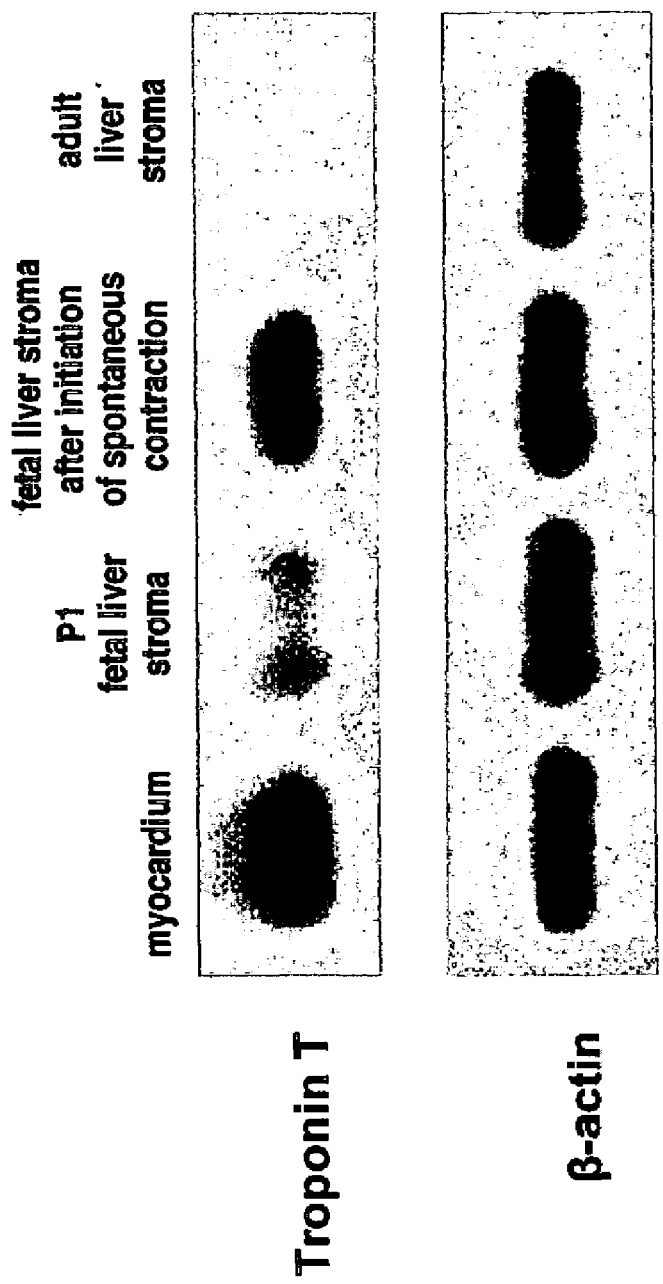
FIG. 12 is a graphical representation of cardiac specific mRNA expression in fetal liver stromal cells after initiation of spontaneous contraction, in accordance with an embodiment of the present invention.
Figure 12C:
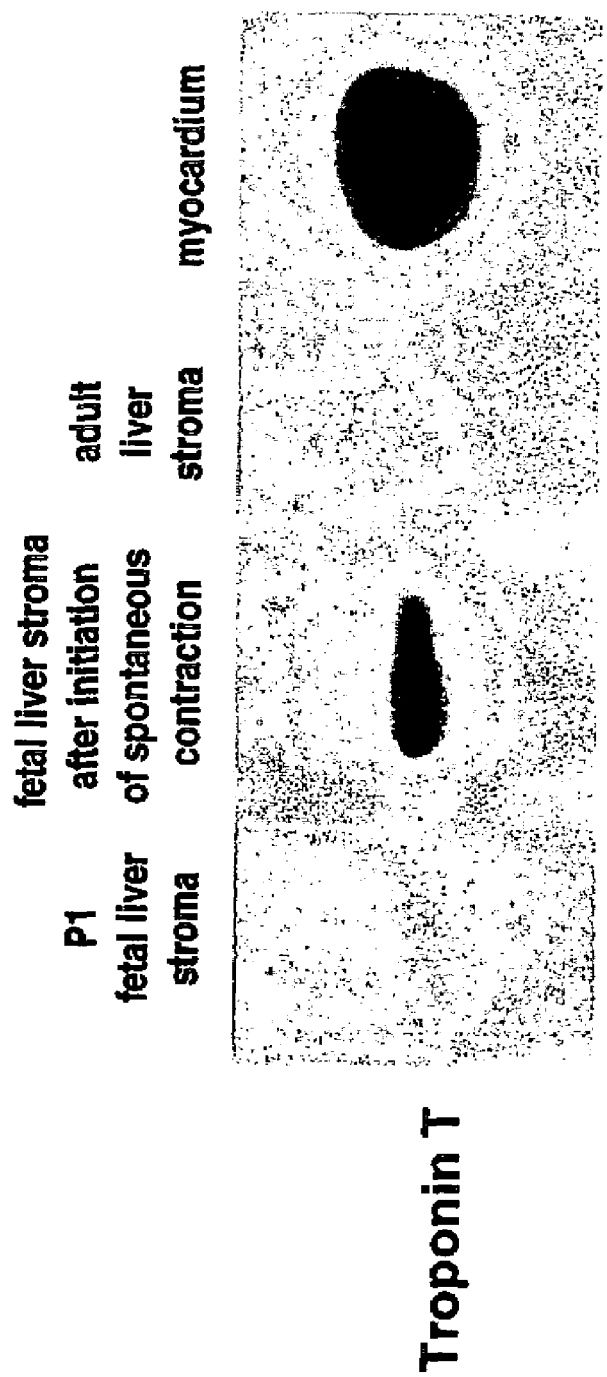

FIG. 12 demonstrates that although present at low levels in early passage undifferentiated fetal liver stromal cells, transcription of mRNA for both atrial natriuretic peptide (FIG. 12*a*) and cardiac troponin T (FIG. 12*b*) was upregulated after initiation of visible spontaneous contraction. De novo translation of troponin T became apparent by Western blotting after initiation of spontaneous contraction (FIG. 12*c*). Equal gel loading was confirmed by BCA protein assay (Pierce, Rockford, Ill.) and Coomassie stain. The observation that cardiac specific mRNA for atrial natriuretic peptide and cardiac troponin T upregulated to levels similar to native myocardium while de novo translation of troponin T could be detected by Western blotting and MEF-2 by immunohistochemistry, further confirmed the myogenic differentiation of the fetal liver stem cells (Orlic D, Kajstura J, Chimenti S, et al. Bone marrow cells regenerate infarcted myocardium, *Nature* 2001; 410 (6829): 701).

No multilineage progenitors could be isolated from adult liver stroma as no chondrogenic (FIGS. 10*e,g*) or myogenic differentiation was noted under any of the above culture conditions. An occasional adipocyte (<2% of cells), however, was seen after adipogenic induction as well as after exposure to dexamethasone and 5-Aza.

Example 6

Construction of Bone Marrow Stroma-Seeded Cell Carriers

To evaluate the potential of bone marrow-derived mesenchymal stem cells to differentiate into cardiac myocytes, and be utilized as a cell source for ventricular tissue engineering, 5-Bromo-2-deoxy-uridine (BrdU) labeled rat stromal cells were seeded within the collagenous matrix of a scaffolding created from PLLA and Gore-Tex® and implanted in vivo. Bone marrow stroma was labeled in vitro at the second or third passage for later identification by adding 100 µg/ml of BrdU containing media to 50% confluent cultures for 48 hours. At the completion of the incubation period the cells were washed, liberated form the tissue culture plastic with 0.25% trypsin in 1 mmol/L (EDTA), resuspended at a concentration of $13 \times 10^7$ cells/mL of the neutralized collagen/Matrigel®b hydrogel liquid as described above and seeded onto constructs fashioned from PLLA/Gore-Tex® at 70 µL per construct. By keeping the neutralized collagen mixture on ice, it retained the consistency of a liquid, allowing for the even distribution of cells added to the mixture. When allowed to polymerize at 37° C. for 10 minutes, the mixture formed a gel and retained these characteristics for the duration of the study. After this 10 minute period, the constructs, seeded with marrow stroma, were transferred to a 100 mm dish containing control media for further incubation.

Immunohistochemistry

Double staining for the detection of nuclear BrdU as well as cytoplasmic proteins was performed with 5-Bromo-2-deoxy-uridine Labeling and Detection Kit II (Boehringer Mannheim, Indianapolis, Ind.) and a monoclonal anti-myosin heavy chain antibody (clone NOQ7.5.4D) (Sigma, St. Louis, Mo.) as well as a monoclonal cardiac anti-troponin C antibody (NCL-TROPC) (Novocastra, Newcastle, UK). After rehydration and microwave antigen retrieval with 0.1 M Na citrate, the 5 µm sections were washed and incubated at 37° C. for 45 minutes with the anti-BrdU antibody resuspended in the supplied dilution buffer at a 1:10 concentration. After washing in Tris-buffered saline the sections were incubated with an anti-mouse secondary antibody conjugated to alkaline phosphatase, the signal was amplified by Vectastain® ABC kit (Vector Laboratories, Burlingham, Ca) and developed with Vector Black Alkaline Phosphatase Substrate Kit II (Vector Laboratories, Burlingham, Ca) yielding a black nuclear precipitate indicating BrdU reactivity. The sections were than double stained for either anti-myosin heavy chain or cardiac anti-troponin C utilizing the Mouse on Mouse (M.O.M.™) Immunoperoxidase Immunodetection Kit to prevent cross reactivity with the anti-BrdU antibody, which is also of mouse origin. Slides stained with anti-myosin heavy chain were developed with Vector® NovaRED™ Substrate Kit giving a red/brown precipitate and slides stained with anti-troponin C were developed with Vector® VIP Substrate Kit producing a violet precipitate. The nuclei were not counter stained and cells containing black nuclei were considered as labeled with BrdU and originating from the transplanted bone marrow stromal cells. Negative controls for this portion of the experiment consisted of stromal cells not labeled in vitro with BrdU and scaffoldings without the seeded stromal cells that were transplanted in an identical manner.

Evaluation of Bone Marrow Stroma Seeded Scaffoldings

Figure 9A:
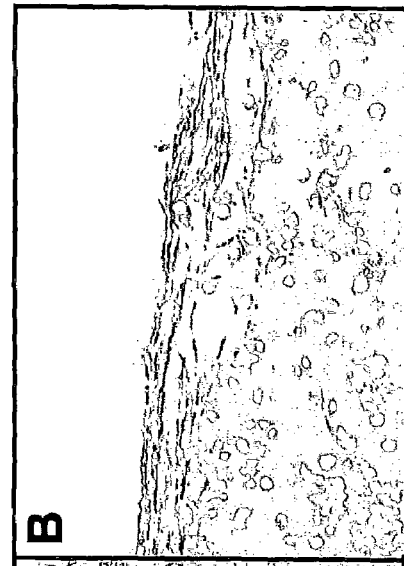
FIG. 9 is a histologic evaluation of bone marrow cells, in accordance with an embodiment of the present invention.
Figure 9B:
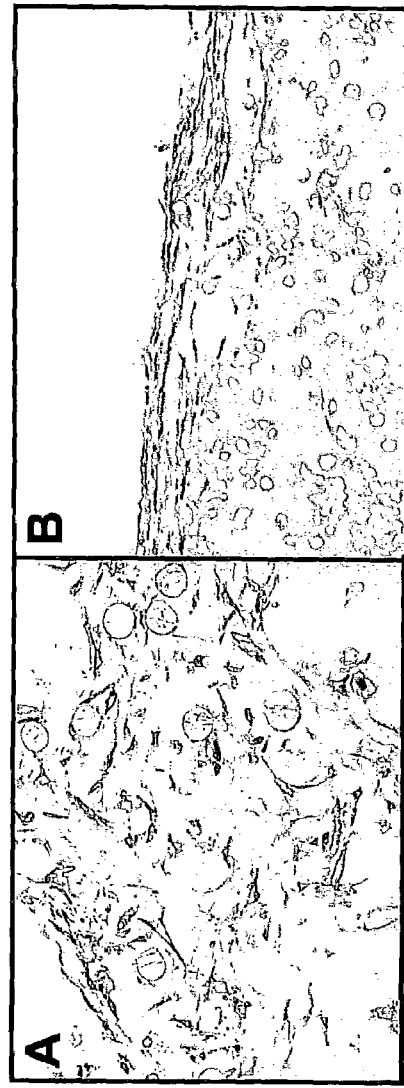
Figure 9C:
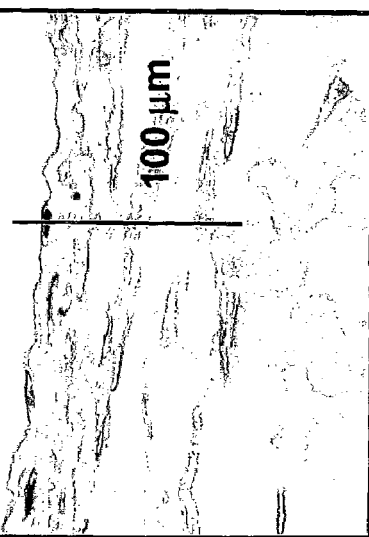

Consistent with previous reports, rat bone marrow stroma within the cultures contained stem cells, which differentiated into adipocytes and osteoblasts under appropriate in vitro conditions (data not shown) (Pittenger M F, Mackay A M, Beck S C, et al. Multilineage potential of adult human mesenchymal stem cells, *Science* 1999; 284: 143-147). Twenty-four hours after seeding bone marrow stroma in a type I collagen hydrogel within a PLLA/polytetrafluoroethylene matrix, the cells had a uniform, viable fibroblast like morphology throughout the construct (200×, H&E) (FIG. 9a). Histologic evaluation after one week in culture on a three-dimensional matrix revealed that cells in the center of the construct developed an apoptotic morphology with cytoplasmic blebbing, distortion of cellular/morphology and pyknotic nuclear degradation. (100×, H&E) (FIG. 9b). Cells at the periphery, within 100 μm of the surface, however, maintained a viable fibroblast-like morphology and retained this appearance for up to one month (400×, H&E) (FIGS. 9b,c). BrdU incorporation was evident in >80% of cells (data not shown).

Example 7

Transplantation of Bone Marrow Stroma-Seeded Cell Carriers

FIG. 13 illustrates a method of surgical implantation of a cell-seeded construct. In brief, after cold cardioplegia and transplantation, but prior to reperfusion of the heterotopic heart, the left ventricle was incised and a three-dimensional type I collagen based stem cell seeded construct was implanted into the ventricle and sutured to the surrounding myocardium.

After overnight incubation a portion of the constructs was cooled to 4° C. and implanted into the left ventricle in order to enlarge the ventricular cavity as described above. The heart were then immediately transplanted into syngeneic recipients by the technique of Ono and Lindsay, creating a non-functioning left ventricle (Ono K, Lindsey E S. Improved technique of heart transplantation in rats, *Journal of Thoracic & Cardiovascular Surgery* 1969; 57: 225-229). Minimal cold ischemic time (<90 minutes) for both the construct and the transplanted heart was maintained throughout the experiment. One month after transplantation, the animals were sacrificed, the hearts fixed in 10% buffered formalin, embedded in paraffin, and sectioned for histology and immunohistochemistry. A portion of the constructs seeded with bone marrow stroma was not implanted in vivo and utilized for in vitro evaluation only. After incubation for either 24 hours, one week, or one month, a representative construct was removed from the incubator, preserved overnight in 10% formalin, embedded in paraffin, cut into 5 μm sections and evaluated histologically.

Figure 14:
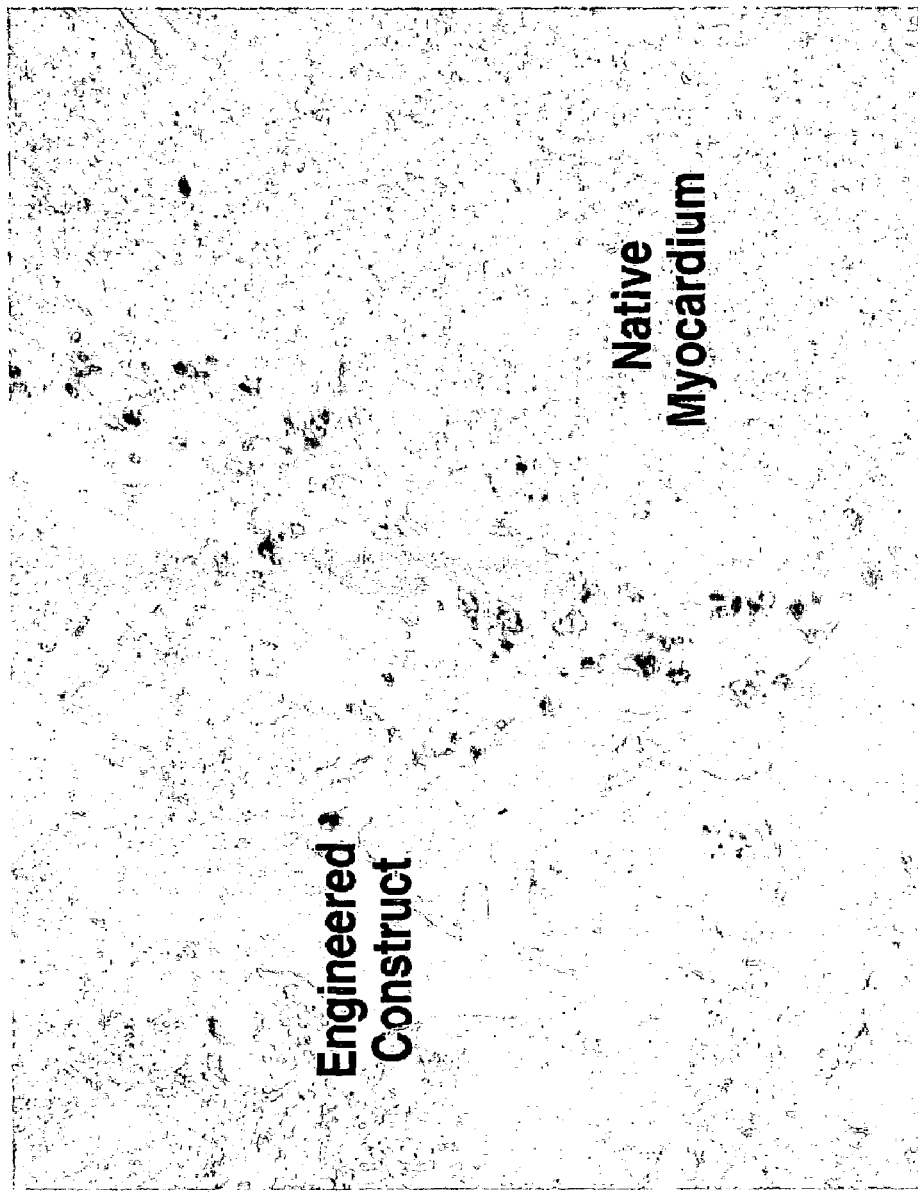
FIG. 14 is a graphic representation of Anti-BrdU immunohistochemistry demonstrating staining at the junction of a cell carrier seeded with bone marrow cells and native myocardium after one month in vivo, in accordance with an embodiment of the present invention.

Hematoxylin and eosin staining of MPC-seeded constructs one month after in vivo implantation revealed no inflammatory response and incorporation of these constructs into the surrounding myocardium similar to those without stem cells. Single step staining for BrdU incorporation revealed reactivity at the junction of native myocardium and the engineered construct in three out of the four animals in this experimental group (200×, H&E) (FIG. 14). No BrdU positive cells were detectable in the center of any construct.

Figure 15A:
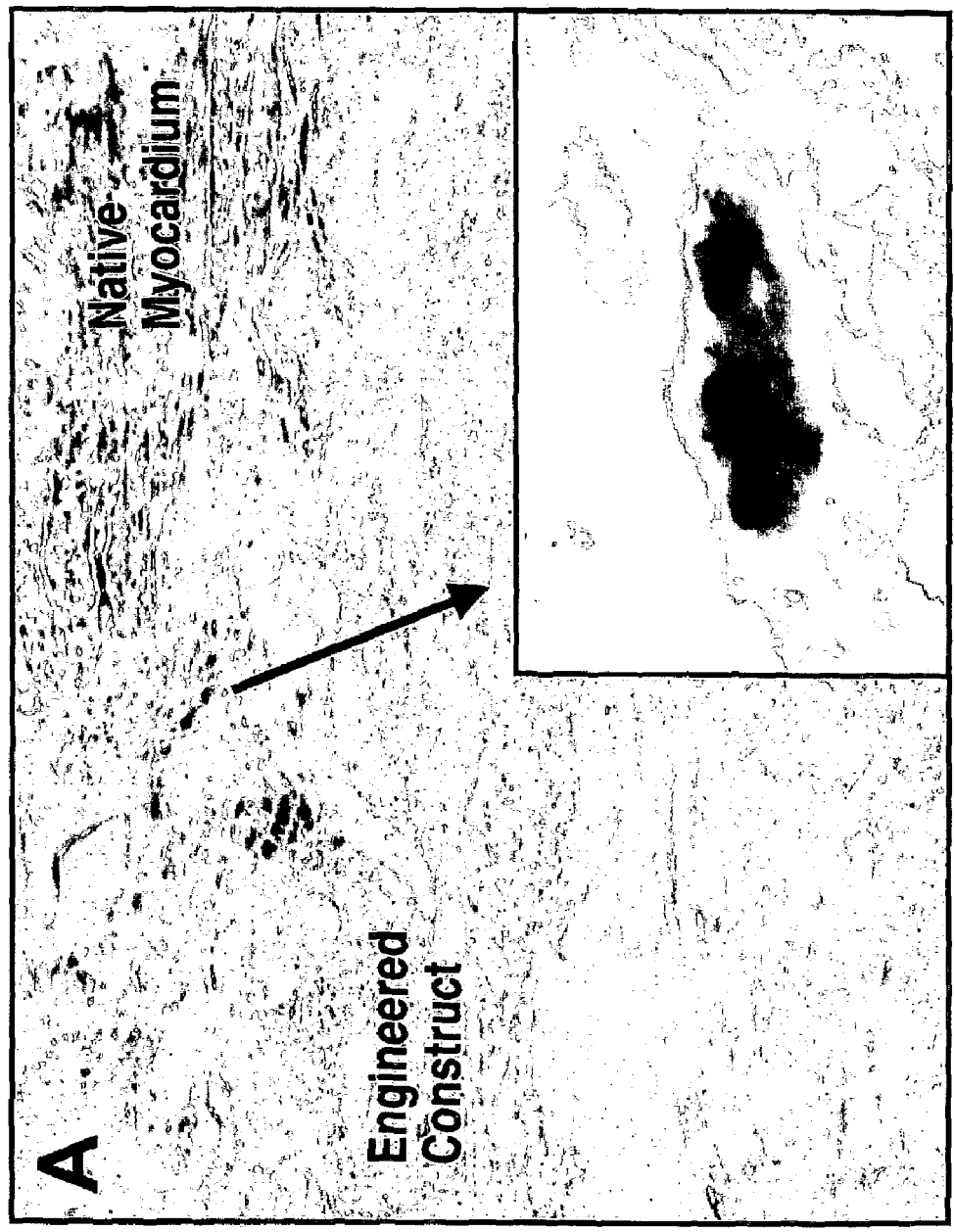
FIG. 15 is a graphic representation of immunohistochemical staining for both BrdU (black) and myosin heavy chain (brown), demonstrating that a portion of the transplanted cells differentiated into myocytes.
Figures 15B, 15C:
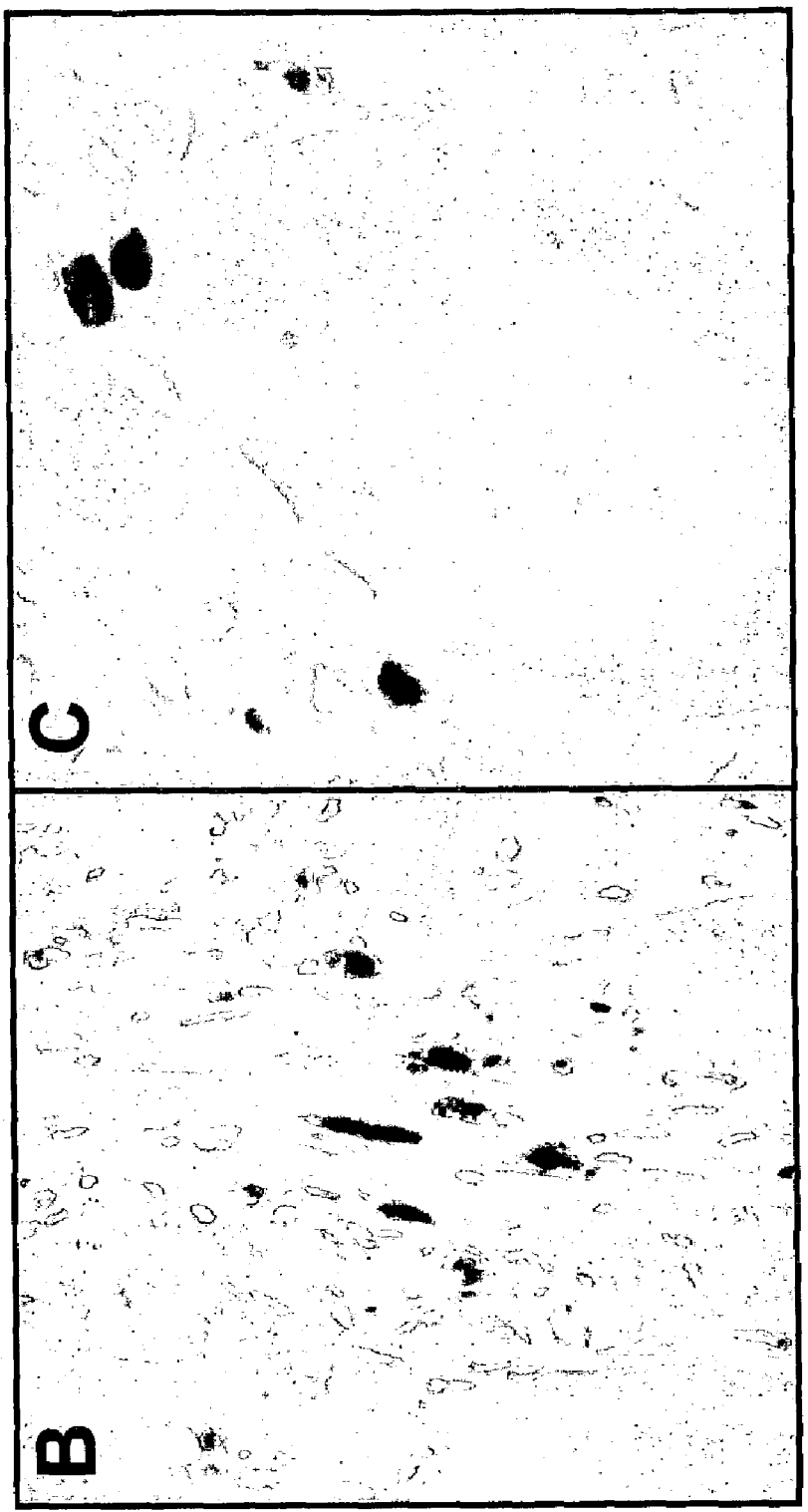
Figure 15D:

FIG. 15 shows double staining for both BrdU (black) and myosin heavy chain (brown). The results indicated that a portion of the cells had differentiated toward the myocytic lineage and expressed cytoplasmic myosin. If visualized longitudinally, the transplanted cells had the characteristic bi-nucleated appearance of cardiac myocytes (200×) (inset 1000× oil immersion) (FIG. 15a). Not all transplanted cells stained for cytoplasmic myosin heavy chain; some formed elongated, multinucleated, cells resembling smooth muscle while others localized to the blood vessel wall, resembling perivascular pericytes (FIG. 15b,c). These findings confirm the multilineage differentiation in the intracardiac environment. Alternatively, this could indicate the heterogeneity of the transplanted bone marrow stroma. Since cardiac myosin heavy chain shares structural similarity to skeletal myosin heavy chain, and both are recognized by the Sigma anti-myosin clone NOQ7.5.4D, evidence supporting cardiomyocytic differentiation of a portion of the transplanted cells was obtained by double staining with cardiac specific anti-troponin C (violet) and BrdU (black) (400×) (inset 1000× oil immersion) (FIG. 15d). No double stained cells were detected in the negative control animals.

Example 8

In vivo application for myocardial tissue engineering using fetal liver cells

In order to evaluate this cell population's utility for myocardial tissue engineering and take advantage of the differentiation cues present within regenerating myocardium, the present inventors transplanted undifferentiated fetal liver stromal cells, organized as a three-dimensional organoid, into the left ventricular wall of immunocompromised adult male nude rats (NIHNU, Taconic Farms, Germantown, N.Y.) utilizing the heterotopic heart transplantation model of left ventricular tissue engineering described herein. Passage one fetal liver stromal cells (2.5×10$^6$) were labeled in vitro with 5-Bromo-2-deoxy-uridine (BrdU) and organized into 1×4×4 mm type I collagen/Matrigel® based three-dimensional organoid reinforced by porous non-woven polylactide mesh (PLLA) (Transome Inc., Palm Bay, Fla.). A donor heart was then transplanted as a vascularized heterotopic infrarenal abdominal graft into an animal from the same colony after sublethal 500 cGy irradiation of the recipients from a cesium source. Immediately prior to reperfusion of the heterotopic heart an organoid containing BrdU labeled fetal liver stromal cells was implanted directly into the left ventricle and sutured to the surrounding myocardium with a running 9-0 nylon suture (US Surgical Corporation, Norwalk, Conn.) (FIG. 13). Two to four weeks after implantation the animals were sacrificed and engraftment and differentiation of the transplanted fetal cells were evaluated as described herein.

In vivo cardiomyocyte differentiation

FIG. 16 shows a diagram and graphical representation of myocardial engineering using a construct seeded with liver stroma stem cells (n=3). (FIG. 16a) is a schematic coronal cross section through the right and left ventricle depicting the placement of the engineered construct. A closer view of this area reveals incorporation and neovascularization of the transplanted tissue (100×H+E) (FIG. 16b). Staining for BrdU labeled cells reveals nuclear staining within the construct (two arrows) and in the immediately adjacent myocardium (single arrow)(200×). Remnants of PLLA fibers, which have not yet dissolved, are evident in the transplanted tissue (FIG. 16c). No BrdU reactivity is evident in constructs seeded with cells that were not labeled with BrdU in vitro indicating the specificity of the stain (FIG. 16d). Double staining for both BrdU and cytoplasmic contractile proteins revealed cardiomyocytic differentiation of the transplanted cells with co-localization of labeled nuclei with cells positive for troponin C (FIG. 16e), troponin T (FIG. 16f) (arrows) as well as a-actinin (data not shown).

Figure 16B:
FIG. 16 is a diagram and graphical representation of myocardial engineering utilizing a cell carrier seeded with liver stromal cells, according to an embodiment of the invention.
Figure 16D:
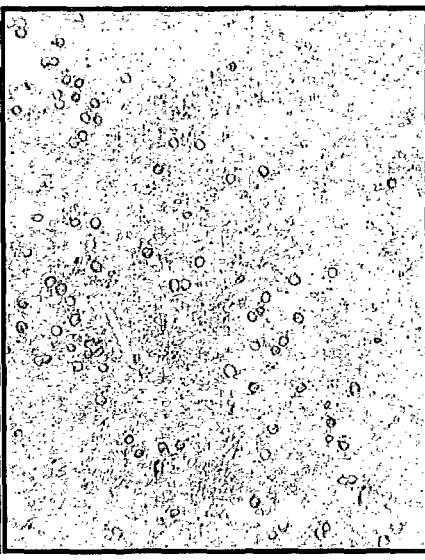
Figure 16A:
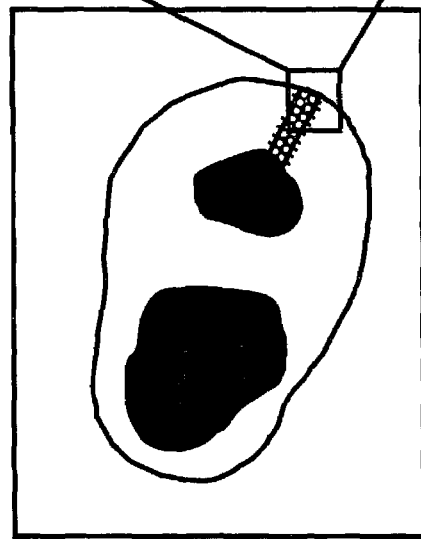
Figure 16C:
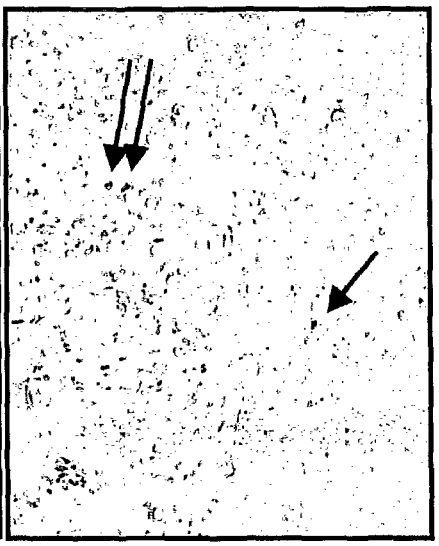

In all animals the stem cell seeded construct (FIG. 16a) had incorporated into the myocardial wall with visible neovascularization (FIG. 16b). Staining for BrdU revealed survival and engraftment of the ovine cells in the transplanted matrix as well as within myocardial tissue immediately adjacent to the matrix (FIG. 16c). The specificity of the BrdU stain was confirmed by the lack of staining in the ovine stem cell seeded constructs implanted without prior BrdU labeling (FIG. 16d). Consistent with the previously described pattern of contractile protein expression utilized to define cardiomyocytic differentiation of adult stem cells, double staining for BrdU and cardiac muscle specific proteins revealed that a portion of the stromal cells in the system had undergone myogenic differentiation with expression of cytoplasmic troponin T, sarcomeric α-actinin, as well as cardiac troponin C, a protein whose expression the present inventors had previously defined as specific for cardiac myocytes (FIG. 16e,f). Unlike skeletal myocytes derived after induction with 5-aza or dexamethasone (FIGS. 11b-e), the engrafted cells were not elongated structures with multiple peripheral nuclei but rounded cells with abundant cytoplasm and centrally located nuclei (FIGS. 16e-f). Between 3-5% of the transplanted cells assumed a cardiac myocyte-like morphology in vivo.

Those skilled in the art will also appreciate that numerous other modifications to the invention are possible within the scope of the invention. Accordingly, the scope of the invention is not intended to be limited to the preferred embodiments described above, but only by the appended claims.

What is claimed is:

1. A cell delivery patch adapted for implantation in the heart of an animal, comprising: a collagen hydrogel layer having tissue cells for delivery and biologically active molecules disposed therein and/or thereon that enable said tissue cells to grow and/or differentiate; an intermediate layer that comprises a biodegradable porous mesh that forms a composite construct with said collagen hydrogel layer; and a reinforcement layer adjacent to said intermediate layer, said reinforcement layer comprising a material extending substantially over a cross-sectional dimension of said patch and having pliancy characteristics whereby it may withstand the forces of the heart during contraction so as to prevent ventricular dilation.

2. The cell delivery patch of claim 1 wherein said collagen comprises at least one of Type I collagen and Type IV collagen.

3. The cell delivery patch of claim 1 wherein said biologically active molecules comprise growth factors that enable said tissue cells to grow and/or differentiate.

4. The cell delivery patch of claim 1 wherein said collagen hydrogel layer further comprises a basement membrane matrix.

5. The cell delivery patch of claim 1 wherein said porous mesh comprises non-woven material.

6. The cell delivery patch of claim 1 wherein said porous mesh comprises biocompatible material.

7. The cell delivery patch of claim 1 wherein said porous mesh comprises biodegradable material.

8. The cell delivery patch of claim 7 wherein said biodegradable material comprises at least one of polyglycolide and polylactide.

9. The cell delivery patch of claim 1 wherein said reinforcement layer comprises slowly biodegradable material.

10. The cell delivery patch of claim 1 wherein said reinforcement layer comprises non-biodegradable material.

11. The cell delivery patch of claim 10 wherein said non-biodegradable material comprises polytetrafluoroethylene.

12. The cell delivery patch of claim 1 having a three-dimensional organoid shape.

13. The cell delivery patch of claim 1 wherein said patch is engineered to replace portions of a heart chamber.

14. The cell delivery patch of claim 13 wherein said patch is engineered to replace portions of a heart ventricle.

15. The cell delivery patch of claim 1 wherein said biologically active molecules comprise a chemokine or cytokine, or a combination thereof.

16. The cell delivery patch of claim 1, wherein said collagen hydrogel has a consistency whereby it may be sutured to myocardial tissue.

17. A cell delivery patch adapted for implantation in the heart of an animal, comprising:
  a collagen hydrogel layer having tissue cells for delivery and biologically active molecules disposed therein and/or thereon, said biologically active molecules enabling said tissue cells to grow and/or differentiate;
  an intermediate layer in contact-with said collagen hydrogel layer, said intermediate layer comprising a porous mesh that forms a composite construct with said collagen hydrogel layer; and
  a reinforcement layer adjacent to said intermediate layer, said reinforcement layer comprising at least one of non-biodegradable material and slowly biodegradable material, said reinforcement layer extending substantially over a cross-sectional dimension of said patch and having pliancy characteristics whereby said reinforcement layer may withstand the forces of the heart during contraction so as to prevent ventricular dilation.

* * * * *

```
                              SEQUENCE LISTING

<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Antisense sequence

<400> SEQUENCE: 1
gatatggagc tgctgtcgc                                                   19

<210> SEQ ID NO 2
<211> LENGTH: 20
<212> TYPE: DNA
<213> ORGANISM: Artificial Sequence
<220> FEATURE:
<223> OTHER INFORMATION: Antisense sequence

<400> SEQUENCE: 2
tgcgtttgca cgccttgcag                                                  20

<210> SEQ ID NO 3
<211> LENGTH: 21
<212> TYPE: DNA
<213> ORGANISM: Artificial Sequence
<220> FEATURE:
<223> OTHER INFORMATION: Antisense sequence

<400> SEQUENCE: 3
ccgtttggag gacaagatgc c                                                21

<210> SEQ ID NO 4
<211> LENGTH: 21
<212> TYPE: DNA
<213> ORGANISM: Artificial Sequence
<220> FEATURE:
<223> OTHER INFORMATION: Antisense sequence

<400> SEQUENCE: 4
tccaatcctg tccatccttc c                                                21

<210> SEQ ID NO 5
<211> LENGTH: 20
```

-continued

```
<212> TYPE: DNA
<213> ORGANISM: Artificial Sequence
<220> FEATURE:
<223> OTHER INFORMATION: Antisense sequence

<400> SEQUENCE: 5
aatgctgggc ctgataaatg                                              20

<210> SEQ ID NO 6
<211> LENGTH: 20
<212> TYPE: DNA
<213> ORGANISM: Artificial Sequence
<220> FEATURE:
<223> OTHER INFORMATION: Antisense sequence

<400> SEQUENCE: 6
ccgaaactcg attccgtaga                                              20

<210> SEQ ID NO 7
<211> LENGTH: 20
<212> TYPE: DNA
<213> ORGANISM: Artificial Sequence
<220> FEATURE:
<223> OTHER INFORMATION: Antisense sequence

<400> SEQUENCE: 7
gaacctgacc tcccactgaa                                              20

<210> SEQ ID NO 8
<211> LENGTH: 20
<212> TYPE: DNA
<213> ORGANISM: Artificial Sequence
<220> FEATURE:
<223> OTHER INFORMATION: Antisense sequence

<400> SEQUENCE: 8
cctctgtcag cttggtcctc                                              20

<210> SEQ ID NO 9
<211> LENGTH: 25
<212> TYPE: DNA
<213> ORGANISM: Artificial Sequence
<220> FEATURE:
<223> OTHER INFORMATION: Antisense sequence

<400> SEQUENCE: 9
atcaccattg gcaatgagcg gttcc                                        25

<210> SEQ ID NO 10
<211> LENGTH: 24
<212> TYPE: DNA
<213> ORGANISM: Artificial Sequence
<220> FEATURE:
<223> OTHER INFORMATION: Antisense sequence

<400> SEQUENCE: 10
ctcgtcatac tcctgcttgc tgat                                         24
```